(12) United States Patent
Oxley

(10) Patent No.: US 10,575,783 B2
(45) Date of Patent: *Mar. 3, 2020

(54) METHODS FOR SENSING OR STIMULATING ACTIVITY OF TISSUE

(71) Applicant: Synchron Australia Pty Limited, Melbourne (AU)

(72) Inventor: Thomas James Oxley, New York, NY (US)

(73) Assignee: Synchron Australia Pty Limited, Parkville (AU)

(*) Notice: Subject to any disclaimer, the term of this patent is extended or adjusted under 35 U.S.C. 154(b) by 0 days.

This patent is subject to a terminal disclaimer.

(21) Appl. No.: 16/164,482

(22) Filed: Oct. 18, 2018

(65) Prior Publication Data

US 2019/0046119 A1 Feb. 14, 2019

Related U.S. Application Data

(63) Continuation of application No. 14/348,863, filed as application No. PCT/AU2012/001203 on Oct. 3, 2012.

(Continued)

(51) Int. Cl.
  *A61N 1/375* (2006.01)
  *A61N 1/05* (2006.01)
  (Continued)

(52) U.S. Cl.
  CPC .......... *A61B 5/6862* (2013.01); *A61B 5/0006* (2013.01); *A61B 5/04001* (2013.01); *A61B 5/0484* (2013.01); *A61B 5/4064* (2013.01); *A61B 5/4076* (2013.01); *A61B 5/4836* (2013.01); *A61B 5/4851* (2013.01); *A61B 5/686* (2013.01); *A61B 5/6868* (2013.01);
  (Continued)

(58) Field of Classification Search
  CPC ... A61B 5/6868; A61B 5/6876; A61B 5/6811; A61B 5/0476–0478; A61N 1/056
  See application file for complete search history.

(56) References Cited

U.S. PATENT DOCUMENTS 6,018,682 A 1/2000 Rise
6,171,239 B1 * 1/2001 Humphrey ........... A61B 5/0482
  600/372

(Continued)

FOREIGN PATENT DOCUMENTS

CN 101137977 3/2008
JP 2007535984 12/2007
  (Continued)

OTHER PUBLICATIONS

Oxley, T. et al. "Minimally invasive endovascular stent-electrode array for high-fidelity, chronic recordings of cortical neural activity," Nature Biotechnology, 34(3):320-327, Feb. 8, 2016.

*Primary Examiner* — Marcia L Watkins
(74) *Attorney, Agent, or Firm* — Levine Bagade Han LLP

(57) ABSTRACT

Methods for sensing or stimulating electrical activity of brain tissue from within an animal vessel by placement of an intravascular device within an animal vessel to control an external device, the intravascular device being adapted to at least one of sense and stimulate activity of brain tissue located outside the vessel proximate the intravascular device.

11 Claims, 18 Drawing Sheets

Related U.S. Application Data

(60) Provisional application No. 61/542,822, filed on Oct. 4, 2011.

(51) Int. Cl.

| | | |
|---|---|---|
| *A61B 5/04* | (2006.01) | |
| *A61B 5/0484* | (2006.01) | |
| *G06F 3/01* | (2006.01) | |
| *A61F 2/72* | (2006.01) | |
| *A61F 2/50* | (2006.01) | |
| *A61B 5/0478* | (2006.01) | |
| *A61B 5/00* | (2006.01) | |
| *A61N 1/36* | (2006.01) | |
| *A61N 1/372* | (2006.01) | |
| *A61N 1/378* | (2006.01) | |
| *A61F 2/54* | (2006.01) | |

(52) U.S. Cl.
CPC .............. *A61B 5/6876* (2013.01); *A61F 2/72* (2013.01); *A61N 1/056* (2013.01); *A61N 1/0553* (2013.01); *A61N 1/36003* (2013.01); *A61N 1/36064* (2013.01); *A61N 1/36067* (2013.01); *A61N 1/36082* (2013.01); *A61N 1/3756* (2013.01); *A61N 1/3787* (2013.01); *A61N 1/37252* (2013.01); *G06F 3/015* (2013.01); *A61B 5/04012* (2013.01); *A61B 5/0478* (2013.01); *A61B 5/4094* (2013.01); *A61B 5/6811* (2013.01); *A61B 5/746* (2013.01); *A61F 2/54* (2013.01); *A61F 2002/5058* (2013.01)

(56) References Cited

U.S. PATENT DOCUMENTS

| | | | |
|---|---|---|---|
| 6,537,310 | B1 | 3/2003 | Palmaz et al. |
| 6,820,676 | B2 | 11/2004 | Palmaz et al. |
| 7,190,998 | B2 | 3/2007 | Shalev et al. |
| 7,647,097 | B2 | 1/2010 | Flaherty et al. |
| 7,751,877 | B2 | 7/2010 | Flaherty et al. |
| 7,881,780 | B2 | 2/2011 | Flaherty |
| 7,901,368 | B2 | 3/2011 | Flaherty et al. |
| 7,991,461 | B2 | 8/2011 | Flaherty et al. |
| 8,060,194 | B2 | 11/2011 | Flaherty |
| 8,095,209 | B2 | 1/2012 | Flaherty |
| 8,386,050 | B2 | 2/2013 | Donoghue et al. |
| 8,560,041 | B2 | 10/2013 | Flaherty et al. |
| 8,812,096 | B2 | 8/2014 | Flaherty et al. |
| 9,220,899 | B2 | 12/2015 | Cattaneo et al. |
| 9,375,330 | B2 | 6/2016 | Sims et al. |
| 2004/0249302 | A1 | 12/2004 | Donoghue et al. |
| 2005/0113744 | A1 | 5/2005 | Donoghue et al. |
| 2005/0137646 | A1 | 6/2005 | Wallace et al. |
| 2005/0137647 | A1* | 6/2005 | Wallace ............... A61N 1/0529 607/45 |
| 2005/0143589 | A1 | 6/2005 | Donoghue et al. |
| 2005/0203366 | A1 | 9/2005 | Donoghue et al. |
| 2005/0251239 | A1 | 11/2005 | Wallace et al. |
| 2005/0267597 | A1 | 12/2005 | Flaherty et al. |
| 2005/0272974 | A1 | 12/2005 | Gavriel |
| 2005/0273890 | A1 | 12/2005 | Flaherty et al. |
| 2006/0049957 | A1 | 3/2006 | Surgenor et al. |
| 2006/0058627 | A1 | 3/2006 | Flaherty et al. |
| 2006/0058854 | A1 | 3/2006 | Abrams et al. |
| 2006/0089709 | A1 | 4/2006 | Helmus |
| 2006/0167564 | A1 | 7/2006 | Flaherty et al. |
| 2006/0189901 | A1 | 8/2006 | Flaherty et al. |
| 2006/0206167 | A1 | 9/2006 | Flaherty et al. |
| 2006/0241356 | A1 | 10/2006 | Flaherty |
| 2006/0253166 | A1 | 11/2006 | Flaherty et al. |
| 2006/0259107 | A1 | 11/2006 | Caparso et al. |
| 2007/0032738 | A1 | 2/2007 | Flaherty et al. |
| 2007/0106143 | A1 | 5/2007 | Flaherty |
| 2007/0142871 | A1 | 6/2007 | Libbus et al. |
| 2007/0156126 | A1 | 7/2007 | Flaherty |
| 2007/0239256 | A1 | 10/2007 | Weber et al. |
| 2008/0009914 | A1 | 1/2008 | Buysman et al. |
| 2008/0015459 | A1 | 1/2008 | Llinas |
| 2008/0027346 | A1* | 1/2008 | Litt .................. A61B 5/0478 600/544 |
| 2008/0118546 | A1* | 5/2008 | Thatcher .................. A61L 27/18 424/426 |
| 2008/0119911 | A1 | 5/2008 | Rosero |
| 2008/0183253 | A1 | 7/2008 | Bly |
| 2009/0131873 | A1 | 5/2009 | Spear et al. |
| 2009/0221896 | A1 | 9/2009 | Rickert et al. |
| 2010/0023021 | A1 | 1/2010 | Flaherty |
| 2010/0063411 | A1 | 3/2010 | Donoghue et al. |
| 2010/0106259 | A1 | 4/2010 | Llinas et al. |
| 2010/0114195 | A1 | 5/2010 | Burnes et al. |
| 2010/0152812 | A1 | 6/2010 | Flaherty et al. |
| 2010/0292602 | A1* | 11/2010 | Worrell ................ A61B 5/0478 600/544 |
| 2010/0305476 | A1 | 12/2010 | Thornton et al. |
| 2013/0090651 | A1 | 4/2013 | Smith |
| 2013/0206454 | A1 | 8/2013 | Cattaneo et al. |
| 2013/0226272 | A1 | 8/2013 | Cattaneo et al. |
| 2013/0231658 | A1 | 9/2013 | Wang et al. |
| 2013/0282084 | A1 | 10/2013 | Mathur et al. |
| 2014/0058528 | A1 | 2/2014 | Contreras-Vidal et al. |
| 2014/0142570 | A1 | 5/2014 | Bakczewitz et al. |
| 2014/0180391 | A1 | 6/2014 | Dagan et al. |
| 2014/0288667 | A1 | 9/2014 | Oxley |
| 2015/0105772 | A1 | 4/2015 | Hill et al. |
| 2015/0230742 | A1 | 8/2015 | Silver |
| 2018/0236221 | A1 | 8/2018 | Opie et al. |
| 2018/0303595 | A1 | 10/2018 | Opie et al. |

FOREIGN PATENT DOCUMENTS

| | | |
|---|---|---|
| JP | 2009519807 | 5/2009 |
| JP | 2009527303 | 7/2009 |
| JP | 2010516384 | 5/2010 |
| JP | 2010516405 | 5/2010 |
| WO | WO 2003/101532 | 12/2003 |
| WO | WO 2005/001707 | 1/2005 |
| WO | WO 2005/046469 | 5/2005 |
| WO | WO 2005/051167 | 6/2005 |
| WO | WO 2005/051189 | 6/2005 |
| WO | WO 2005/065738 | 7/2005 |
| WO | WO 2005/092183 | 10/2005 |
| WO | WO 2005/107852 | 11/2005 |
| WO | WO 2005/110528 | 11/2005 |
| WO | WO 2006/015002 | 2/2006 |
| WO | WO 2006/020794 | 2/2006 |
| WO | WO 2006/041738 | 4/2006 |
| WO | WO 2006/073915 | 7/2006 |
| WO | WO 2006/074029 | 7/2006 |
| WO | WO 2006/076164 | 7/2006 |
| WO | WO 2006/076175 | 7/2006 |
| WO | WO 2006/078432 | 7/2006 |
| WO | WO 2006/086086 | 8/2006 |
| WO | WO 2006/105478 | 10/2006 |
| WO | WO 2007/058950 | 5/2007 |
| WO | WO 2007/078410 | 7/2007 |
| WO | WO 2007/146060 | 12/2007 |
| WO | WO 2008/019384 | 2/2008 |
| WO | WO 2008/094345 | 8/2008 |
| WO | WO 2008/094789 | 8/2008 |
| WO | WO 2009/135075 | 11/2009 |
| WO | WO 2010/078175 | 7/2010 |
| WO | WO 2013/049887 | 4/2013 |
| WO | WO 2017/070252 | 4/2017 |
| WO | WO 2018/195083 | 10/2018 |

\* cited by examiner

METHODS FOR SENSING OR STIMULATING ACTIVITY OF TISSUE

CROSS-REFERENCE TO RELATED APPLICATIONS

This application is a continuation of U.S. patent application Ser. No. 14/348,863 filed Mar. 31, 2014, which is a U.S. national application filed under 35 U.S.C. 371 of International Application No. PCT/AU2012/001203 filed Oct. 3, 2012, which claims benefit of priority to U.S. Provisional Application No. 61/542,822 filed Oct. 4, 2011, the contents of which are incorporated by reference herein in their entireties.

TECHNICAL FIELD

In a particular aspect, the present invention may relate to intravascularly sensing or stimulating electrical activity of neural tissue.

BACKGROUND ART

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and broad consistory statements herein.

The ability to sense or stimulate nervous tissue in an animal confers many therapeutic, analytic, and diagnostic advantages or opportunities, some of which may become apparent on further reading of this specification.

Without being an admission of common general knowledge, current techniques for measuring electrical activity of the brain involve the use of extra-cranial electrodes placed on the scalp, or intra-cranial electrodes surgically implanted on the outer cortical surfaces of the brain, or in the epidural or subdural spaces.

Unfortunately there are significant disadvantages associated with these current methods. For example, there may be a lack of clarity or predisposition to disturbances such as noise or movement when using extra cranial electrodes applied externally on the scalp.

Further, when using intra cranial electrodes, there is a requirement for invasive surgery to be performed. This carries considerable risk of complications such as infections or bleeding, and only provides access for electrode placement on the outer surfaces of the brain, at least without cutting into and damaging the brain.

Relocation of an implanted electrode may be required where further investigation of a different region of the brain is desired, or where the signal from the electrode has deteriorated due to scar formation about the site of implantation. However, there are also difficulties associated with relocation of electrodes due to the requirement for further invasive surgery and possible entrapment of the electrode in scar tissue.

Current intra cranial electrodes can also require a direct electrical connection to computer equipment which is located external to the patient's body.

Thus, it may be advantageous to provide a new method or means for sensing or stimulating neuronal cells or neural tissue which reduces, limits, overcomes, or ameliorates some of the problems, drawbacks, or disadvantages associated with prior art devices or methods, or provides an effective alternative to such devices or methods.

DISCLOSURE OF THE INVENTION

In one aspect the invention may provide an intravascular device for placement within an animal vessel, the intravascular device being adapted to sense or stimulate activity of neural tissue located outside the vessel proximate the intravascular device.

The neural tissue may comprise neuronal cells. The device may be adapted to sense or stimulate activity of one or more neuronal cells.

The intravascular device may comprise a sensor adapted to sense activity of neural tissue located outside the vessel proximate the intravascular device.

The intravascular device may comprise a stimulator adapted to stimulate activity of neural tissue located outside the vessel proximate the stimulator.

Thus, the intravascular device may comprise at least one of a sensor and a stimulator for respectively sensing or stimulating activity or neural tissue located outside the vessel proximate the intravascular device.

The intravascular device, or sensor or stimulator thereof, may comprise an electrode. The electrode may be adapted to engage the wall of the vessel. The electrode may protrude slightly from the outer surface of the intravascular device.

The electrode may comprise an inert substance. The inert substance may comprise platinum or nitinol. The use of an inert substance may allow deposition of the electrode within the vessel for several years, or the remainder of the animal's life.

There may be multiple electrodes. For instance, there may be a plurality of electrodes arranged in 2 times.4 array.

The intravascular device, or the sensor thereof, may be adapted to sense local field potentials from proximate neural tissue. Additionally, or alternatively, the intravascular device, or the sensor thereof, may be adapted to sense electrical activity of a single neuron of the proximate neural tissue. Thus the intravascular device may be adapted to sense an action potential of a neuronal cell.

The intravascular device, or the stimulator thereof, may be adapted to stimulate a local field potential in proximate neural tissue. Additionally, or alternatively, the intravascular device, or stimulator thereof, may be adapted to stimulate electrical activity of a single neuron of the proximate neural tissue. Thus the intravascular device may be adapted to stimulate an action potential in a neuronal cell.

The electrode may be disposed on a mounting member. The mounting member may comprise the electrode. The mounting member may be adapted to conduct electrical signals. Thus, the mounting member may comprise an electrically conductive member.

The intravascular device may comprise the mounting member. The mounting member may comprise silicone.

Suitably, the mounting member may be encased in a stable substance. The stable substance may encase the mounting member and electrode. The stable substance may comprise silicone.

The mounting member may comprise a board. The board may be encased in silicone. The board may comprise a printed circuit board.

The mounting member may comprise a flexible flap. The flexible flap may comprise silicone.

The mounting member may comprise a wire, or a wire may be disposed on the mounting member. There may be a plurality of wires.

The intravascular device may comprise a microchip. The microchip may be electrically connected to the electrode. The wire may extend between the electrode and the microchip.

The microchip may comprise a microprocessor.

The microchip may comprise a channel amplifier.

The microchip may comprise a digital signal converter.

The microchip may comprise an RF transmitter/receiver.

The wire may extend from the electrode to an external device located outside of the body of the animal. There may be multiple wires extending from multiple electrodes. The wires may congregate to form a bundle which passes out of the body of the animal.

In another aspect, the invention may provide a retainer for retaining the intravascular device at a position within the vessel. The intravascular device may be disposed on the retainer The retainer may be expandable. The retainer may comprise a stent. The stent may comprise a mesh framework. The stent may be expandable to take the shape of the surrounding vessel.

The stent may comprise a biodegradable or bioabsorbable substance. The stent may be gradually broken down inside the body.

Alternatively, the stent may comprise an inert substance such as nitinol or platinum. Thus the stent may remain functional in the body for several years, or even the lifetime of the animal.

The retainer may comprise a probe. The probe may comprise an elongate flexible micro-tube.

The stent may be adapted to expand when ejected out of an end of the probe. The stent may be adapted to contract when retracted into the probe. Thus the stent may be adapted to be deployed, retrieved, and re-deployed. The redeployment may take place at a different region within the vessel to that of the earlier deployment.

In another form, the intravascular device may be mounted on the probe. The stent may be absent in such an embodiment. The probe may be adapted to conduct electrical signals to or from the intravascular device. The probe may comprise a guide wire or cable. The electrode wires may electrically connect with the guide wire or cable.

The retainer may comprise an adhesive substance adapted to cause adhesion of the intravascular device to the inside of the vessel wall. The adhesive substance may be present on an outer surface of the intravascular device.

In another aspect, the invention may provide a system for sensing or stimulating activity of neural tissue comprising an intravascular device for placement within an animal vessel, the intravascular device being adapted to sense or stimulate activity of neural tissue located outside the vessel proximate the intravascular device.

The system may further comprise a guide member for guiding the intravascular device to a region within the vessel proximate the neural tissue to be sensed or stimulated.

The guide member may be adapted for passing into and through the animal vessel. The guide member may be adapted for passage of the intravascular device therethrough.

The guide member may comprise a catheter. Thus, the intravascular device may be passed through the catheter to a region within the vessel proximate the neural tissue to be sensed or stimulated.

The catheter may be flexible. The external diameter of the catheter may be less than 3 millimetres. The internal diameter of the catheter may be greater than 0.5 mm.

The system may comprise a retainer or retaining member for retaining the intravascular device at a region within the vessel proximate the neural tissue to be sensed or stimulated. The retaining member may be adapted for passage through the guide member.

The system may comprise an electronic system.

The electronic system may comprise an electrode of the intravascular device, and an electrically conductive member connected with the electrode.

The electronic system may comprise a processor. The processor may be located within or without the body of the animal. For example, in one embodiment the processor is an internal processor in the form of a microprocessor which is mounted on the intravascular device, whereas in another form the electrodes are electrically connected to an external processor such as a computer. In yet another form, the processor may be an internal processor in the form of a microprocessor which is mounted on a unit located in the body separately to the intravascular device. The processor may comprise a channel amplifier.

The processor may comprise a digital signal converter.

The processor may comprise an RF transmitter/receiver.

The processor may comprise at least one of an internal processor disposed on the intravascular device, and an external processor which is present outside the body.

A wireless form of the intravascular device may comprise the internal processor. The internal processor may comprise a channel amplifier, digital signal converter and RF transmitter/receiver.

A non-wireless version of the intravascular device may comprise the external processor. The external processor may comprise the channel amplifier and the digital signal converter. The RF transmitter/receiver may be absent in the non-wireless version. This omission may be made due to power being directly received from an external power source, or signals being directly transmitted through a solid medium such as a wire. Thus, the system may comprise a unit. The unit may be located separately to the intravascular device. The unit may be located internally or in the body. In a particular form, the unit may be located subcutaneously in the pectoral region. There may be more than one internal unit. Additionally or alternatively, the unit may be located externally. For instance, the unit may be mounted on the patient's head. Thus, the system may comprise at least one of an internal unit and an external unit. Where there is an internal unit, an external unit may be paired for wireless coupling therewith.

The external unit may be adapted to communicate wirelessly with the internal unit. The external unit may be adapted for placement about a region of the body adjacent the internal unit.

The unit may be connected by an elongate electrically conducting member, such as a wire, to the intravascular device. The electrically conducting member may run substantially through the vasculature between the unit and the intravascular device.

It may be that the internal unit, or one of the internal units, is connected by wire to the intravascular device, whereas the external unit, or one of the external units, is electrically connected to an external device. The external device may comprise at least one of a computer, stimulation box, and prosthetic limb.

The unit may comprise a retaining mechanism for retaining the unit in the desired position. The retaining mechanism may comprise suture holes. The unit may comprise a power source. Power may be transferred wirelessly from the external unit to the internal unit. The wireless energy transfer may occur via electromagnetic induction. The power source may comprise a pair of conducting members adapted to be inductively coupled. The internal unit may comprise one of the conducting members and the external unit may comprise the other.

The internal unit may comprise a data transfer mechanism for wireless transfer of data to the external unit. In a particular form, the data may be transferred via the electromagnetic coupling. In another form, an RF transmitter/receiver may be used for wireless data transfer to the external unit.

The system may comprise alignment means for aligning the external unit with the internal unit or intravascular device. The alignment means may comprise a magnetic element. There may be a pair of magnetic elements cooperatively disposed on the external unit and the internal unit or intravascular device.

Additionally or alternatively, the power source may comprise at least one of a battery or capacitor and RF transmitter/receiver.

The unit may comprise a microchip. The microchip may comprise a microprocessor with signal amplifier and multiplexor.

The system may comprise a wireless transmission system for wirelessly transmitting at least one of data and energy to or from the intravascular device.

The wireless transmission system may comprise at least one of a magnetic induction coil and an RF transmitter/receiver.

The system may comprise an alert system. The alert system may be adapted for signaling an alert when the sensed activity of neural tissue falls outside of a predetermined parameter.

The alert may comprise a warning signal which is activated when sensed electrical activity indicates possible imminent onset of seizure in the animal.

The system may comprise a device located separately to the intravascular device, the device being adapted for at least one of storage, processing, and transmission of data or energy to or from the intravascular device. The device may be directly connected to the intravascular device by a solid transmitting medium such as a wire or fiber optic cable. Additionally or alternatively, the intravascular device and the device may be wirelessly linked.

The device may comprise a wireless transmission mechanism for transmitting at least one of data and energy between the intravascular device and the device, or between two devices.

The device may comprise an internal device. The internal device may comprise an internal unit. The internal unit may be adapted for intravascular deposition. In another form, the internal unit may be adapted for subcutaneous deposition.

The device may comprise an external device. The external device may comprise an external unit adapted for placement on or outside the body.

The external device may comprise a computer.

The device may comprise a prosthetic limb.

There may be multiple devices of same or different forms.

The system may further comprise alignment means for aligning the intravascular device, or internal device, with an external device. The alignment means may comprise a pair of magnetic members cooperatively disposed on the intravascular device, or internal device, and the external device.

The system may comprise multiple intravascular devices retained at various regions in one or more animal vessels. Thus, electrical activity of various regions of neural tissue proximate the intravascular devices may be sensed or stimulated.

In another aspect the invention may provide an apparatus for sensing or stimulating activity of neural tissue comprising:

an intravascular device for placement within an animal vessel, the intravascular device being adapted to sense or stimulate activity of neural tissue located outside the vessel proximate the intravascular device, and a retaining member for retaining the intravascular device at a region within the vessel.

The animal vessel may comprise an artery, vein, or lymph vessel.

The animal vessel may comprise a mammalian vessel. In a particular aspect, the mammalian vessel may comprise a human vessel.

The human vessel may comprise a cerebral vessel. For instance, the human vessel may comprise the anterior, middle, or posterior cerebral artery.

In a particular form, the human vessel may comprise the second or third branches of the middle cerebral artery which track along the post central gyms of the brain.

In another aspect, the mammalian vessel may comprise a sheep vessel. The sheep vessel may comprise the superior sagittal sinus.

The vessel may be between 1 and 5 millimeters in diameter at the region where the intravascular device is to be retained. In a particular form, the vessel may be about 3 millimeters in diameter at the region where the intravascular device is to be retained.

The neural tissue may comprise brain tissue.

The brain tissue may comprise the post central gyrus. The brain tissue, or post central gyms, may comprise the motor homunculus.

The brain tissue may comprise the pre central gyms. The brain tissue, or pre central gyrus, may comprise the sensory homunculus.

Thus, depending on the position of the intravascular device or devices, various regions of the brain may be sensed or stimulated, including the pre central gyrus and the post central gyms. This means that imagined movements of limbs or other parts of the body may be sensed when sensing activity of the pre central gyrus, or movements of the limbs or other parts of the body may be activated when stimulating the post central gyms.

Intravascular sensing of the electrical activity of various regions of the brain may be used for monitoring epileptic patients and detecting seizure focus points.

Intravascular stimulation of brain tissue may allow for preoperative brain mapping.

Intravascular deep brain stimulation may be used in the treatment of medical conditions. The medical conditions may include Parkinson's Disease, Depression, Obsessive Compulsive Disorder or Tourette's syndrome. Suitably, intravascular stimulation of deep brain tissue may be used in the treatment of conditions including Parkinson's disease, depression or Obsessive Compulsive Disorder.

The system may comprise a brain computer interface (BCI).

In another aspect the invention may provide a method for sensing or stimulating electrical activity of neural tissue from within an animal vessel.

The method may comprise using an intravascular device to sense or stimulate the electrical activity of the neural tissue from within an animal vessel proximate the neural tissue.

The electrical activity may comprise a local field potential.

The electrical activity may comprise an action potential. The electrical activity may comprise activity of a single neuron.

The method may comprise guiding the intravascular device to a region within the vessel proximate the neural tissue to be sensed or stimulated. The intravascular device may be guided through a catheter.

The method may comprise visualizing the vessel by a medical imaging technique in order to facilitate guidance of the intravascular device to the region of the vessel. The medical imaging technique may comprise angiography.

The method may comprise retaining the intravascular device at the region of the vessel. The intravascular device may be retained against the inner wall of the vessel. The method may comprise expanding a stent to retain the intravascular device against the vessel wall. The method may comprise gradual biological decomposition of the stent.

The method may comprise gradual biological incorporation of the intravascular device into the vessel wall. The intravascular device, or retaining member, is still considered to be 'in' the vessel when incorporated into the vessel wall or projecting into the vessel wall from within the vessel.

The method may comprise endothelialisation of the intravascular device into the vessel wall. The method may comprise scarring of the intravascular device into the vessel wall.

The method may comprise amplifying a signal sensed by the intravascular device.

The method may comprise converting the signal from analogue to digital.

The method may comprise monitoring the signal. The signal may be monitored external to the animal. The signal monitored may comprise an intravascular electroencephalographic (EEG) signal.

The method may comprise powering the intravascular device wirelessly. The intravascular device may be powered by passive induction.

The intravascular device may be powered by radio waves. The method may comprise using radiofrequency identification to transfer data.

The method may comprise long term deposition of the intravascular device in the animal vessel. The intravascular device may be deposited in the animal vessel for multiple years. It may be deposited in the animal vessel for the remainder of the animal's lifetime.

The method may comprise sensing or stimulating electrical activity of neural tissue from various regions in one or more animal vessels. Thus, the electrical activity of various regions of neural tissue may be sensed or stimulated.

The neural tissue may comprise a deep brain region. Thus, the method may comprise sensing or stimulating electrical activity of a deep brain region from within an animal vessel.

The method may comprise retaining or depositing the intravascular device within an animal vessel proximate a deep brain region.

The method may comprise detecting epileptic seizures, or the focus thereof, by monitoring intravascular EEG activity.

The method may comprise mapping quantities or properties of sensed or stimulated neural tissue. A property may comprise function. Thus, the method may comprise mapping the function of sensed or stimulated neural activity. The method may comprise brain mapping. The method may comprise stimulating deep brain tissue in order to map its function.

The method may comprise stimulating deep brain tissue for treatment of a medical disorder. The disorder may comprise Parkinson's disease, depression, or obsessive compulsive disorder.

The method may comprise sending signals from the neural tissue to a computer. The computer may receive signals relating to the electrical activity of the neural tissue.

The method may comprise sending signals from a computer to the neural tissue. These signals may be sent in response to the signals received. The neural tissue may receive command signals from the computer which excite the neural tissue.

The computer may be comprised of or by an external device.

The method may comprise sending signals from the neural tissue to an external device. These signals may be sent in response to signals received by the neural tissue. The neural tissue may receive command signals from the external device which excite the neural tissue.

The external device may comprise an input device such as a keyboard or mouse. Thus an input device may be controlled by the animal.

The external device may comprise a prosthetic limb. Movement of the prosthetic limb may occur in response to neural tissue activity. Activation of neural tissue may occur in response to stimulation, such as movement or touch, of the prosthetic limb.

The method may comprise wirelessly transmitting data or energy between the intravascular device and a separate device adapted for storing, processing, or transmitting signals to or from the device.

The method may comprise retaining or depositing the intravascular device within an animal vessel proximate a deep brain region. Electrical activity of the deep brain region may be sensed or stimulated.

The method may comprise retaining or depositing the intravascular device in a vessel traversing the hippocampus. This may allow detection of seizures or imminent seizure threat.

The method may comprise sensing changes in electrical activity in the pre central gyrus resulting from attempted movement of natural, absent, or artificial body parts.

The method may comprise causing movement of a natural or artificial body part by intravascularly stimulating the pre central gyms.

The method may comprise placing an external unit over a region of the body proximate the intravascular device, or over a region of the body proximate an internal device linked to the intravascular device, in order to facilitate wireless transmission between the external device and the intravascular device, or between the external device and the internal device.

In another aspect, the invention may provide use of an intravascular device to sense or stimulate electrical activity of neural tissue from within an animal vessel proximate the neural tissue.

BRIEF DESCRIPTION OF THE DRAWINGS

Illustrative but non-limiting embodiments of the invention will now be described with reference to the drawings wherein.

MODES FOR CARRYING OUT THE INVENTION

Figure 1:
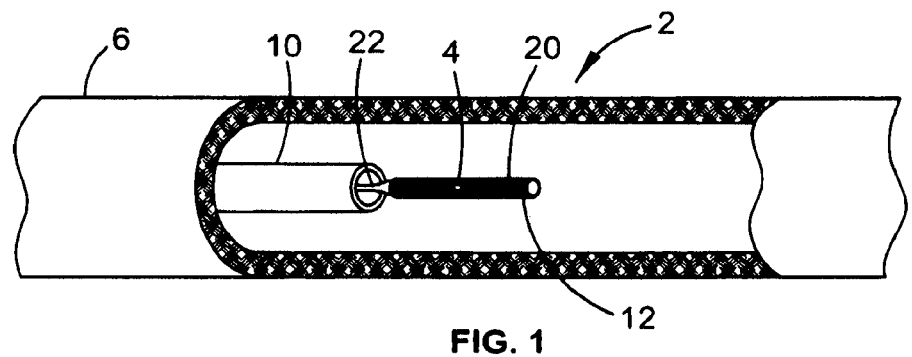
FIG. 1 is a diagram showing a section of the second branch of the middle cerebral artery of a human prior to deposition of a wireless version of an intravascular device with stent.

Referring to the drawings, there is shown a system, generally designated 2, for sensing or stimulating activity of neural tissue 54, such as brain tissue 192. The system 2 comprises an intravascular device 4 for placement in an animal vessel 6, such as the second branch 166 (see FIG. 22) of the middle cerebral artery 160 of a human being 8. A wireless version of the intravascular device 4 is shown in FIGS. 1-5 & 10, and a wired version of the intravascular device 4 is shown in FIGS. 6 to 9.

The system 2 further comprises a retainer 12 for retaining the intravascular device at a region within the artery 6, and a flexible micro-catheter 10 which is to be passed up through the subject's vascular system and allows passage of the intravascular device 4 therethrough.

Figure 3:
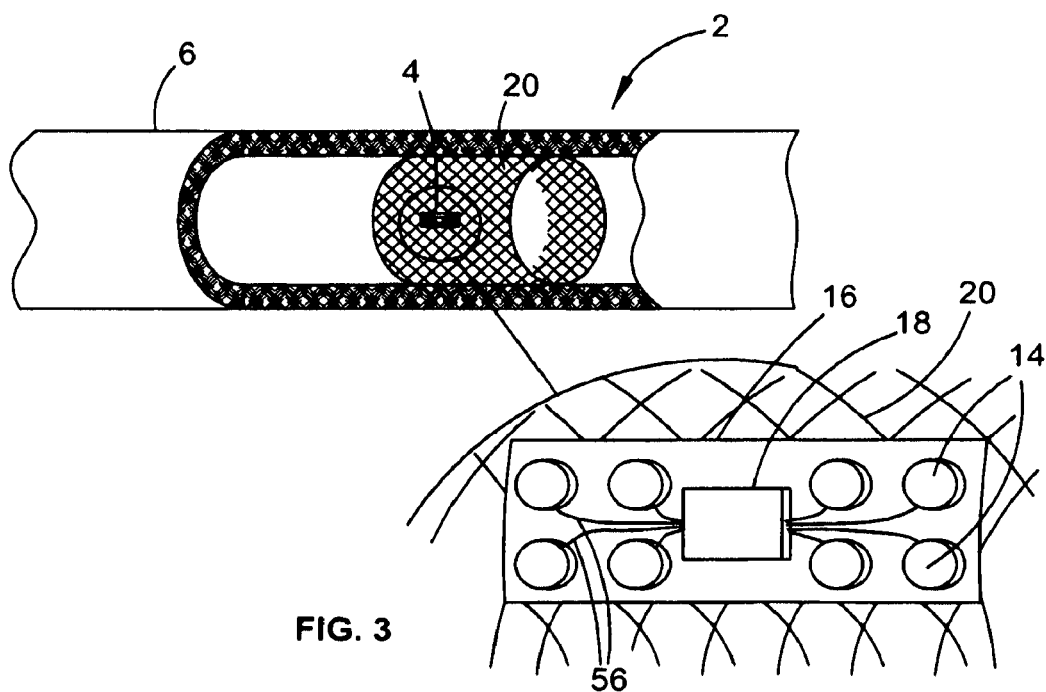
FIG. 3 is a diagram showing the same region of the middle cerebral artery as FIG. 1 with the stent and the intravascular device deposited in the middle cerebral artery, and objects required for insertion and deployment removed; the magnified portion shows the intravascular device and expanded stent.
Figure 4:
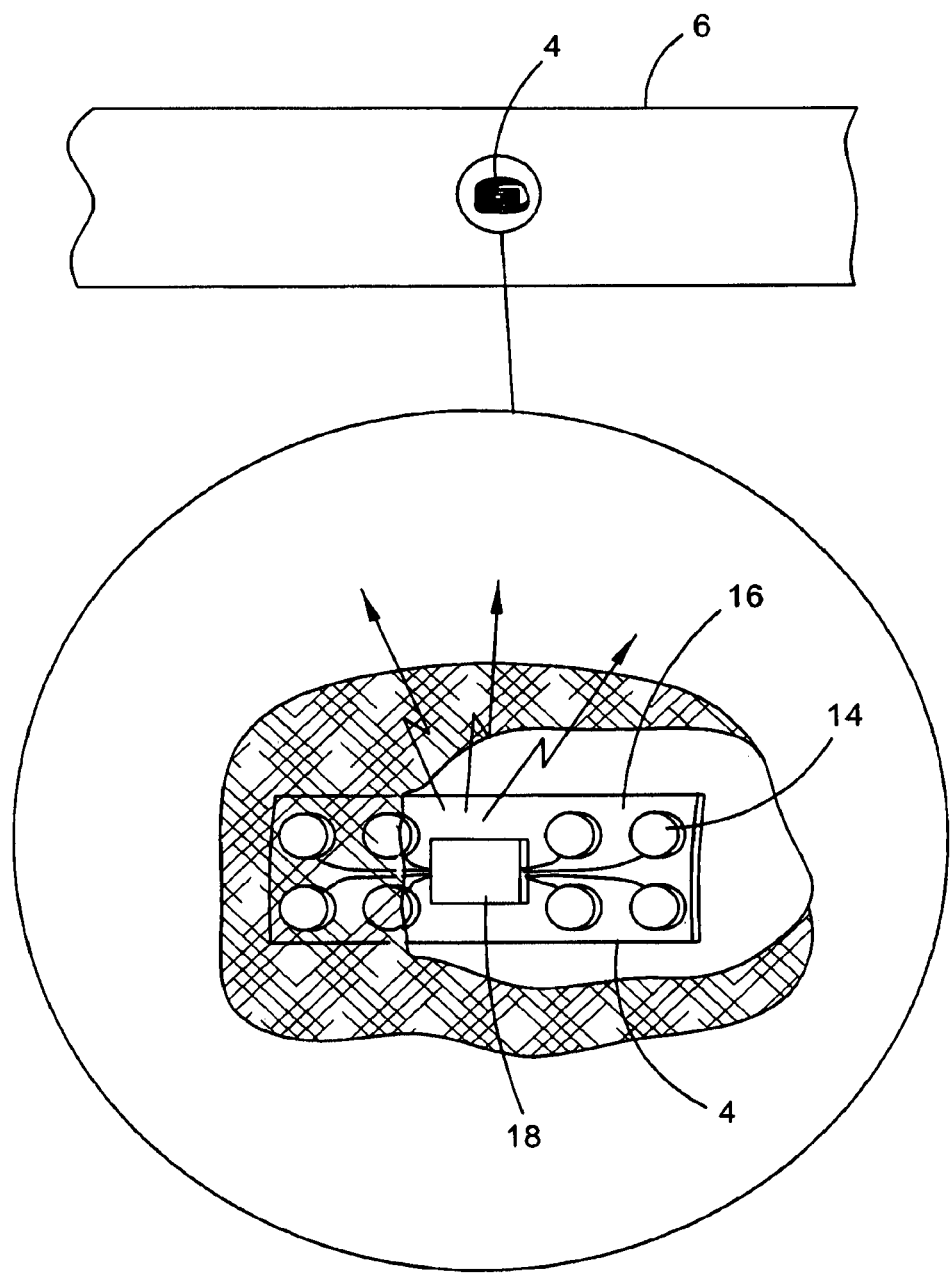
FIG. 4 is a diagram with a magnified portion showing the intravascular device fused with the arterial wall, and the stent absent due to biological decomposition.
Figure 5:
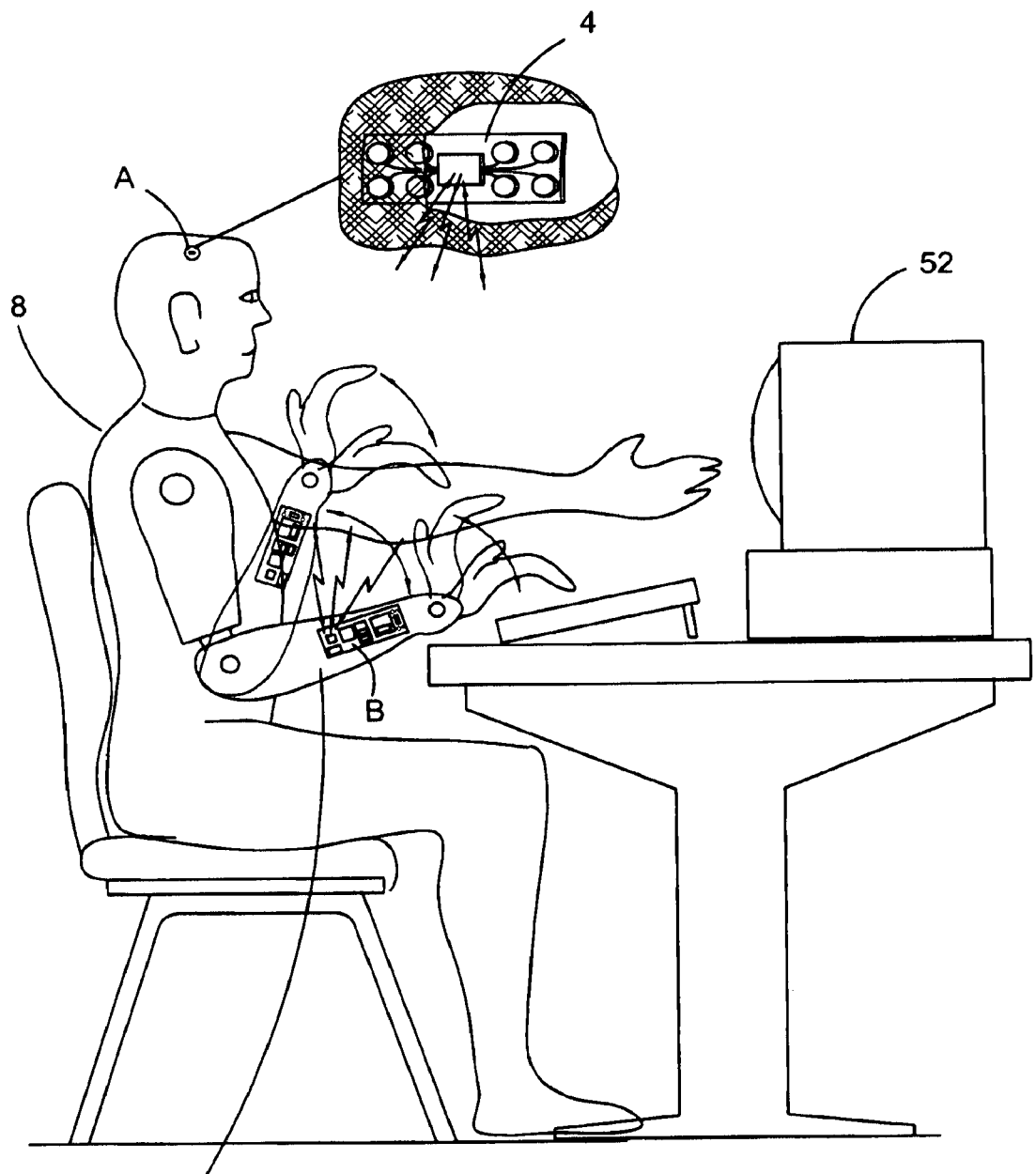
FIG. 5 is a diagram showing how the intravascular device acts as a brain computer interface with a prosthetic limb of a human being.

As shows more clearly in FIG. 3, the wireless version of the intravascular device 4 comprises a 2 times 4 array of circular electrodes 14.

The electrodes 14 are mounted on and project from the outer surface of a rectangular semiconductor board 16 which in this instance is in the form of a soft printed circuit board in a silicone encasement.

Located centrally on an outer surface of the board 16, between two 2 times 2 arrays of electrodes 14, is a rectangular shaped microchip 18. The microchip 18 is electrically connected to each of the electrodes 14 by electrode wires 56.

Figure 7:
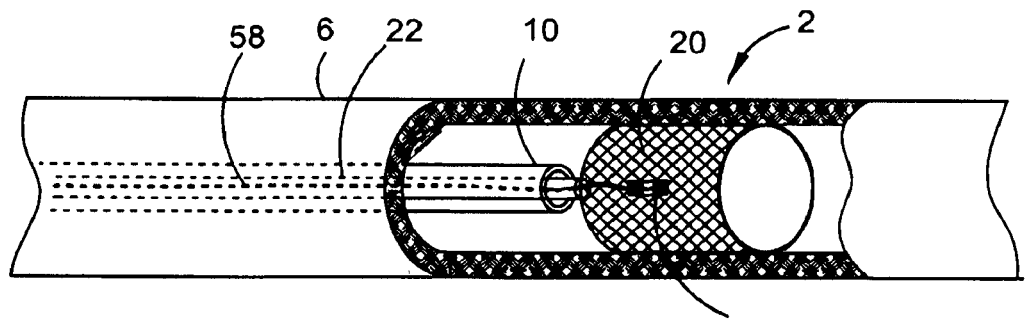
FIG. 7 is a diagram of the section of the middle cerebral artery shown in FIG. 6, with the stent expanded and the intravascular device retained against the arterial wall.
Figure 8:
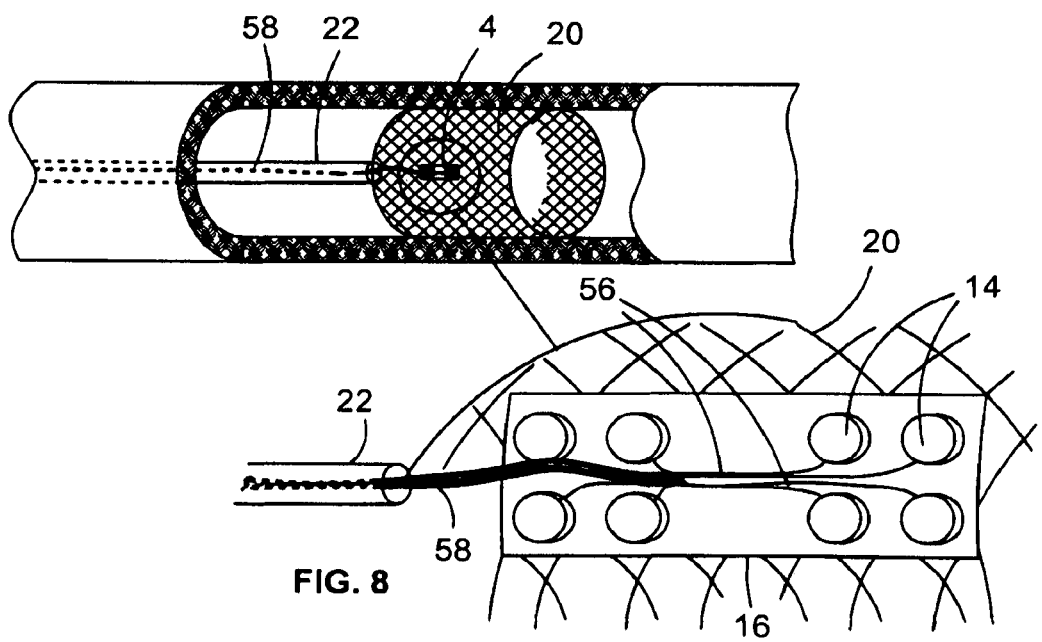
FIG. 8 is a diagram showing the same region of the middle cerebral artery as FIG. 6 with the stent and the intravascular device deposited in the middle cerebral artery and objects required for insertion and deployment removed; the magnified portion shows the intravascular device, expanded stent, and wire bundle which connects externally.
Figure 9:
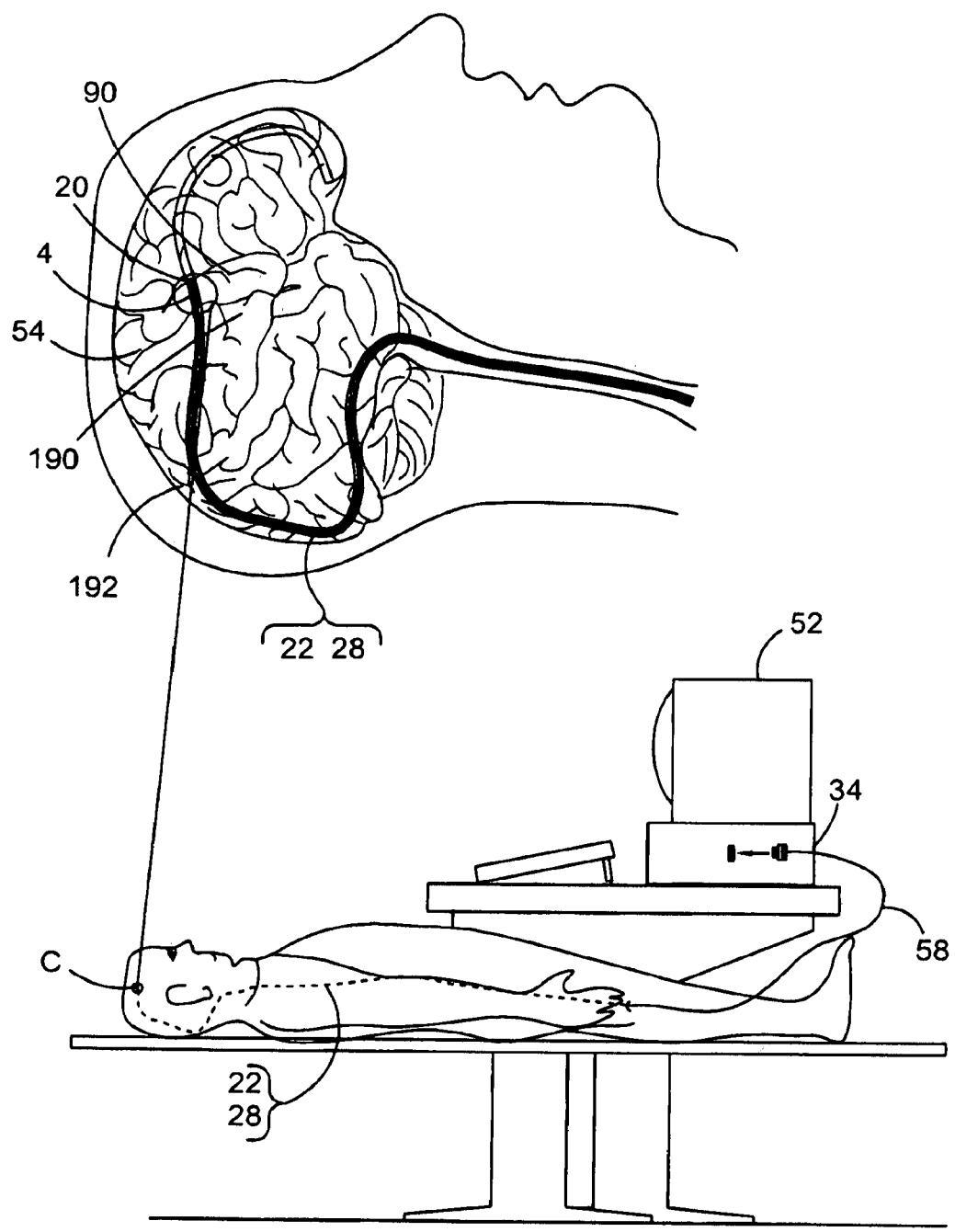
FIG. 9 is a diagram showing the arterial pathway for insertion of an intravascular device adjacent brain tissue; a wired version of the device is shown.

In the wired embodiment shown in FIGS. 6 to 9, the microchip is omitted and the electrode wires 56 congregate to form a wire bundle 58 which extends back through the vascular system and connects with an external computing device 52 (see FIG. 9). Thus, in the particular wired version of the intravascular device 4 shown, the external computing device 52 performs the processing functions that the microchip 18 carries out in the wired version.

Figure 2:
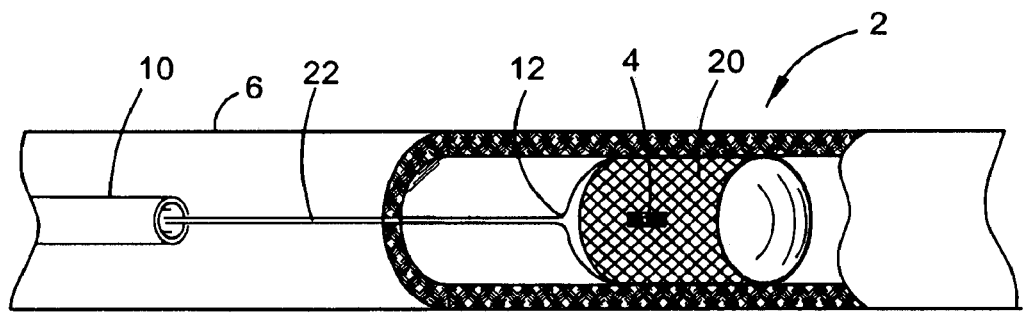
FIG. 2 is a diagram of the section of the middle cerebral artery shown in FIG. 1, with the stent expanded and the intravascular device retained against the arterial wall.
Figure 6:
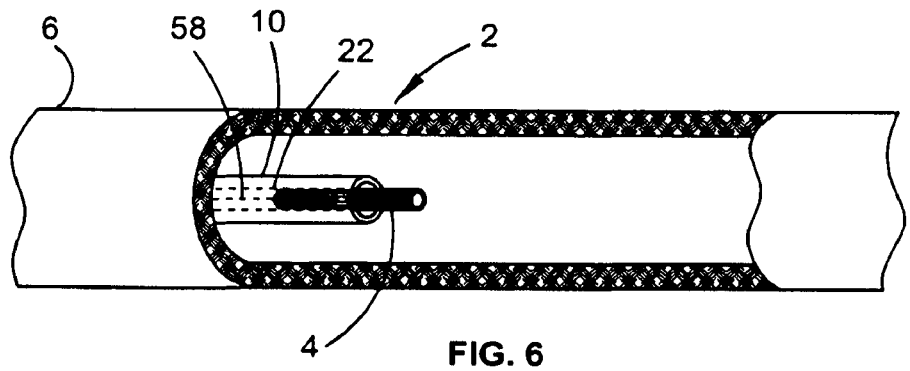
FIG. 6 is a diagram showing a section of the second branch of the middle cerebral artery of a human prior to deposition of a wired version of an intravascular device with stent.

The retainer 12 comprises a stent 20 and a flexible micro-tube probe 22 which, in FIGS. 1 & 2, is attached to the stent at one end, and in FIGS. 6 & 7, acts as a housing for the stent when the stent is in a contracted and retracted state.

The stent 20 has a mesh configuration or lattice framework, and is made of a bio absorbable substance which breaks down gradually in the body, such as over a period of one to two years when deposited into a human vessel. In alternative embodiment the mesh stent is made of an inert metallic substance which can remain functional in teh body for several years or the live of the person.

The stent 20 as shown in FIGS. 6 to 8 is biased to expand. Thus, when the stent 20 is retracted in the micro-tube 22 it conforms to the inner wall of the micro-tube 22, and when it is ejected from the proximal end of the micro-tube it expands, conforming to the shape of the inner arterial wall (assuming the diameter of the inner wall of the vessel is less than that of the stent). The stent takes on a tubular shape when allowed to fully expand. As shown in FIG. 8, the electrodes 14 have a surface that extends parallel to a surface of the stent structure where expansion of the stent does not expand or alter the shape of the electrode surface of each of the electrodes 14.

The semi-conductor board 16 is mounted on the outer mesh surface of the stent 20 so that when the stent is expanded to take the shape of the vessel, the electrodes 14 of the intravascular device 4 are brought into contact with the inner wall of the artery 6.

The guide catheter 10 has an internal diameter of about 0.15 mm which is enough to enable the passage of the micro-tube 22 with retracted stent and intravascular device therethrough.

Figure 13:
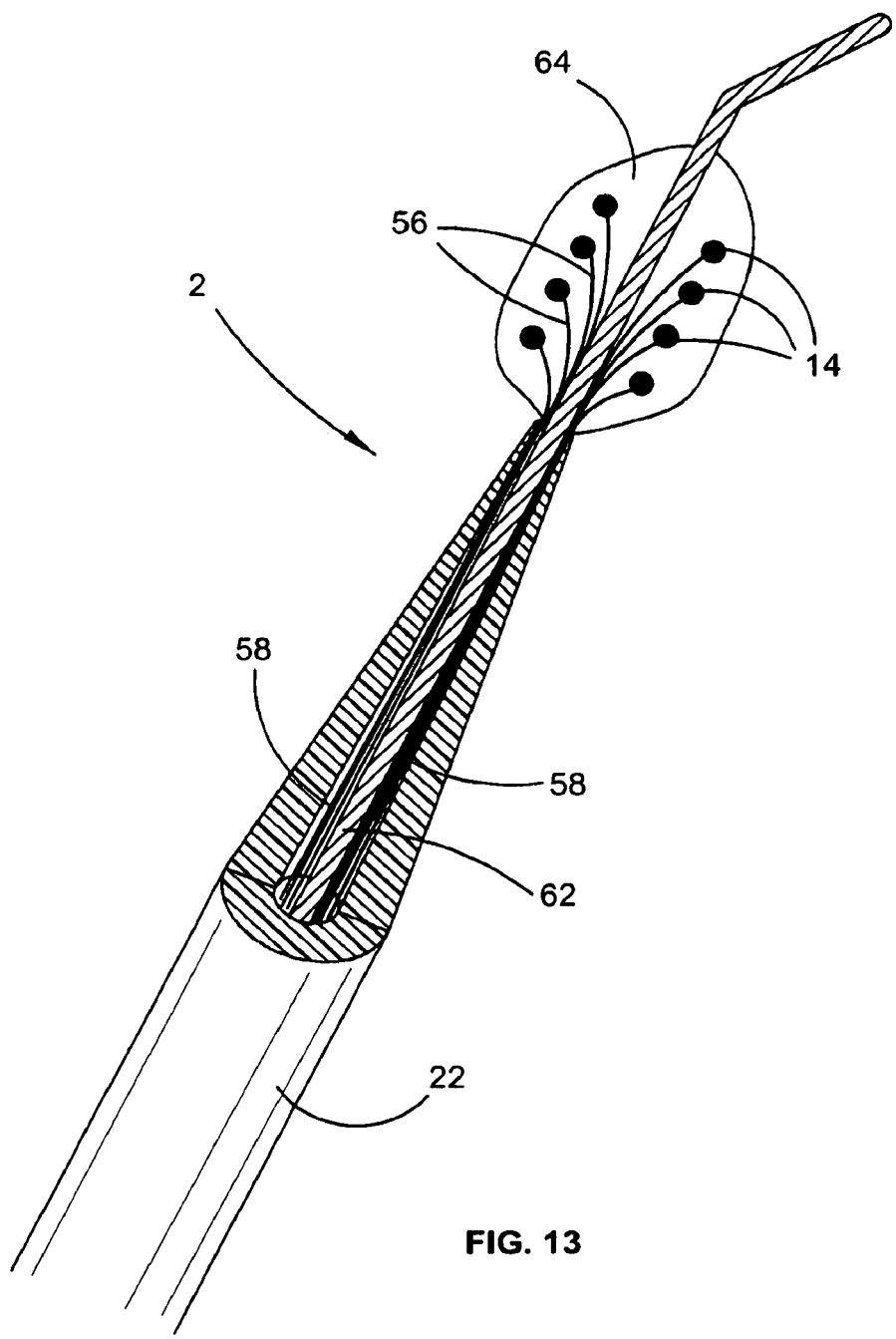
FIG. 13 is a diagram of a further wired version of an intravascular device having an elongate probe with guide wire passing therethrough.

FIG. 13 shows a wired version of the system 2 wherein the intravascular device 4 comprises a 2 times 4 array of electrodes 14 encased in a silicone flap 64.

The silicone flap 64 is mounted at the end of an elongate tubular shaped silicone probe 22. Passing centrally through the probe is a guide wire 62 and wire bundles 58. The wire bundles are formed from individual wires 56 which extend from respective electrodes which are attached to but insulated from the guide wire 62.

The guide wire passes out of the patient's body to external processing equipment 34. As signal processing occurs externally, there is no need for a microchip to be present in this version of the intravascular device.

A wired system 2 such as that shown in FIG. 13 may be used to sense or stimulate neural tissue in order to determine an appropriate location for deposition of a wireless version of the intravascular device.

The intravascular device 4 may be inserted and retained in the desired region of a vein or artery 6 by performing the following steps:

A radio opaque contrast agent is injected into the blood vessel 6 through which the catheter 10 is to be inserted. In this instance, the contrast agent is injected into the femoral artery or internal jugular vein in order to visualize blood vessels and organs of the body using an imaging technique such as radiography, CT and MR angiography.

The catheter 10 is then threaded into and through the femoral artery, and further up through continuing branches of the femoral artery until it reaches the desired position in the second branch of the middle cerebral artery (see FIG. 9 for vascular pathway of catheter). Alternatively, the catheter is threaded into branches of the venous system, initially entering the internal jugular vein up through the branches until entering the superior sagittal sinus and desired position within the cortical veins.

If not already present within the catheter 10, the micro-tube 22 with intravascular device 4 and stent 20 is threaded up through the catheter 10 to proximate the region where the intravascular device is to be retained (see FIG. 6).

The stent 20 is then protruded beyond the proximal end of the micro-tube 22 which has housed it to this point. As the stent 20 is protruded beyond the end of the micro-tube 22 it expands to take on the shape of the blood vessel wall 6, thereby retaining the intravascular device 4 against the inner wall of the vessel 6.

In another form of the invention, the catheter 10 is omitted from the system 2 and the micro-tube 22 acts as both the guide for the stent through the vasculature, as well as the housing for the stent before deposition.

Where long term deposition of the stent 20 is intended, the micro-tube 22 may be detached and separated from the stent 20. A voltage may be delivered to a discrete metallic area interconnecting the micro-tube and the stent, thereby causing induced thermal fatigue of the discrete area and detachment of the stent.

If a new location of the intravascular device is desired, the stent with intravascular device may be withdrawn back into the micro-tube 22, and the system 2 moved to a desired region where redeployment of the stent with intravascular device may then take place.

For long term deposition of the intravascular device, the catheter and detached micro-tube are withdrawn back through and removed from the femoral artery, leaving the stent and intravascular device retained at the desired arterial region.

In a wired version of the device, a device wire 58 formed from a bundle of wires 56 extending from the electrodes 14 may remain in the body during use of the intravascular device 4 (see FIGS. 8 & 9). In one form, the device wire 58 may extend from the intravascular device all the way to and through the femoral artery where it exits the body and attaches to external monitoring or stimulating equipment (see FIG. 9) for short term recording and monitoring during the angiography procedure. Suitably, for longer term recording or monitoring, the device wire may extend from the intravascular device, back through the vasculature to a peripheral blood vessel such as the subclavian artery when the intravascular device is retained in the arterial system or the subclavian vein when the intravascular device is retained in the venous system. At this point, the wire exits through the vessel wall and into the subcutaneous tissue of the pectoral region where it attaches to an internal unit 68 (see FIG. 14).

In one form, the stent biologically decomposes gradually over time, leaving only the intravascular device in place, and the intravascular device is gradually endotheliolised into the inner wall of the artery.

In another form, the stent is made of an inert material, such as platinum or nitinol which is resistant to decomposition, thereby leaving the stent to be incorporated along with the intravascular device into the arterial wall by a process of endothelialisation and/or scarring.

Depending on its location and function, neural tissue of the brain adjacent the intravascular device may be stimulated, or electrical activity in this tissue may be changed, in various manners including:

By the patient actively moving a part of their body. For example, a patient's active movement of their right arm may result from electrical activity in the area of the motor homunculus representing the arm in the pre central gyms 90 of the brain. In such instances, one or more intravascular devices retained or deposited in a portion of the middle cerebral artery or cortical veins adjacent to the motor homunculus may sense electrical activity such as electroencephalography, local field potentials or action potentials in this area of the brain.

By the patient attempting active movement of a part of their body which is no longer present or to which neural connection has been lost. For example, where a patient has had their right arm amputated, attempts to move their absent right arm may still produce a change in electrical activity in the arm portion of the motor homunculus despite the arm not being present.

By part of the patient's body being passively moved by an external force. For example, a physical therapist may passively move a patient's right arm without any active muscle contraction performed by the patient. Such passive movement may cause increased activation of part of the sensory homunculus in the post central gyms 190 relating to arm joint proprioception and skin sensation, as well as sensory feedback resulting from the pressure and warmth of the therapist's hands.

Figure 10:
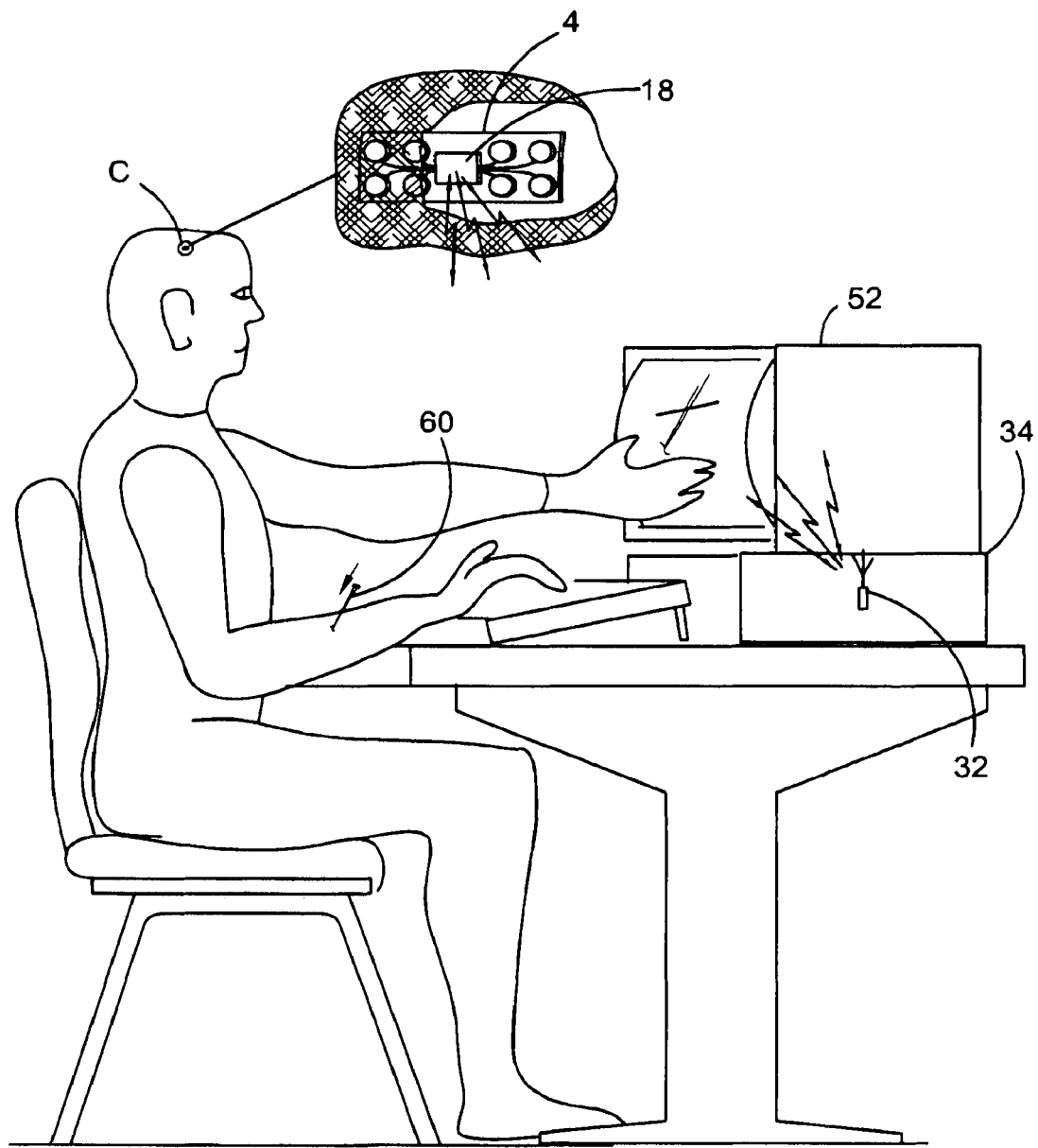
FIG. 10 is a diagram showing a wireless version of the intravascular device deposited in the brain, with the intravascular device transmitting to and receiving signals from an external computing and monitoring device.

By pricking the patient's forearm with a pin 60, thereby causing a change or increase in electrical activity in the sensory portion of the brain associated with touch and pain in the hand (see FIG. 10).

By the patient imagining, remembering or performing a new mental activity, thereby causing electrical activity to be produced in various regions of the brain.

By the patient developing an epileptic seizure. A foci of electrical activity that sparks a seizure within brain tissue may be detected with accurate spatial localisation by changes in electroencephalography using one or more intravascular devices near the area of seizure focus.

By involuntary intrinsic processes. For example, changes in electrical activity in regions of the brain may result from conditions or disease processes such as epilepsy, Parkinson's disease, depression and Obsessive Compulsive Disorder. Deep brain activity may be particularly affected by such conditions.

Figure 11:
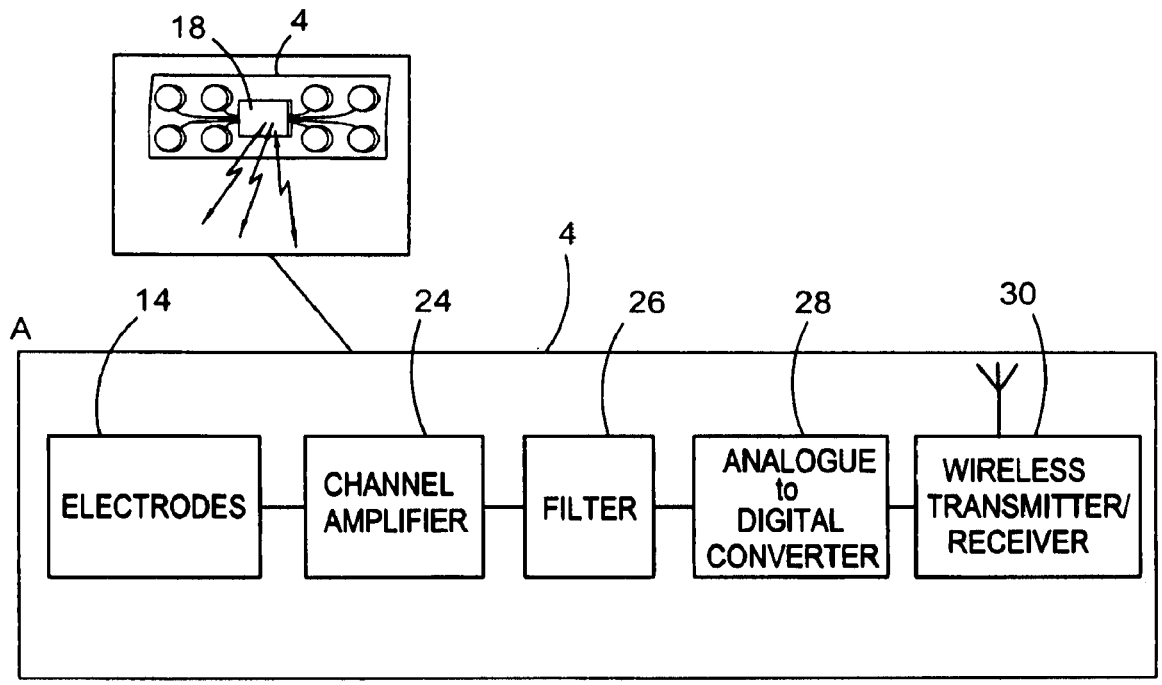
FIG. 11 is a block diagram of the front end electronics of a wireless version of the intravascular device which is to be located within an animal vessel.
Figure 12:
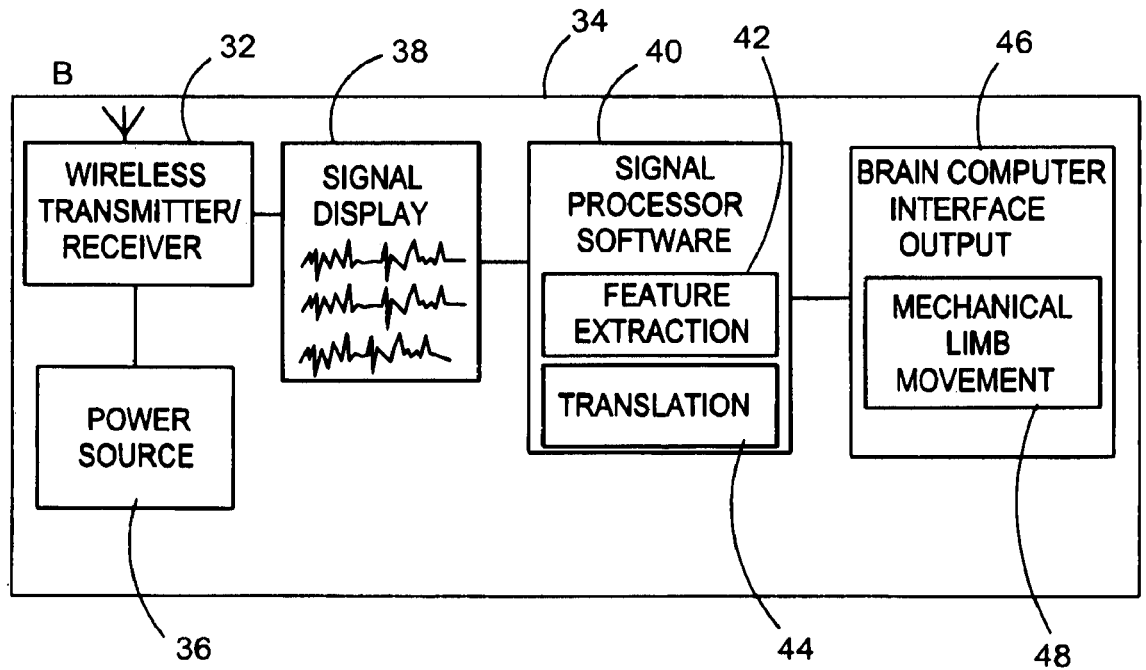
FIG. 12 is a block diagram of the back end electronics of a wireless version of the intravascular device to be located external to the body of the animal.

Once retained in the vessel, the intravascular device 4 may be used to sense the electrical activity, or changes in the electrical activity, of adjacent extra vascular neural tissue, and the electrical activity may be processed, in the following manner:

The electric charge emitted from the stimulated or pathological adjacent neural tissue is sensed and collected by the electrodes 14, and conducted by wires 20 to the microchip 18 (see FIG. 3). As shown in FIG. 11, the microchip houses a channel amplifier 24, filter 26, analogue to digital converter 28, and an RF transmitter/receiver 30.

The signal from the electrodes 14 is passed to the channel amplifier 24 which amplifies the signal from the electrodes.

The amplified signal is converted from analogue to digital by the converter 28.

A microprocessor controlled induction coil or RF transmitter 30 then transmits the digital signal wirelessly to a corresponding induction coil or RF receiver 32 which forms part of an external processing system 34, such as a computer. The computer 34 also comprises a power source 36, a signal display 38, signal processor software 40 which is adapted to perform feature extraction 42 and translation 44, and a brain computer interface output 46 which in this instance is adapted to cause mechanical limb movement 48 of a prosthetic limb 50. The signal display 38 is in the form of an intravascular EEG signal which is displayed on a monitor 52.

The intravascular EEG signal may be processed by software which enables feature extraction and translation for a brain computer interface. The resultant BCI output 46 enables the patient to control operation of devices in the external environment. This may include movement of mechanical limbs 48 and control of computer inputting devices such as mice or keyboards.

Monitoring the display signal may enable detection and diagnosis of conditions in the brain, such as the detection of epileptic seizures or parameters which indicate that a seizure is imminent. Further, detection and monitoring of conditions such as Parkinsons disease, depression, and Obsessive Compulsive Disorder may be achieved by monitoring intravascular EEG signals from adjacent deep brain regions.

Once retained or deposited in the artery 6, the intravascular device may be used to stimulate regions of adjacent neural tissue in the following manner:

In the wireless version of the device 4, a signal is sent by the external RFID receiver 32 and received by the RF transmitter/receiver 30 of the intravascular device. The signal may be sent in response to a signal transmitted by the intravascular device 4 to the external computer 34, with the response to the transmitted signal being determined by the signal processor software 40.

The signal is then transmitted from the RF transmitter/receiver 30 to the electrodes in a form which may then be further transmitted to the adjacent neural tissue, thereby causing excitation or activation of a local field potential or action potential in the adjacent neural tissue.

Intravascular neural stimulation may have various applications such as in preoperative mapping whereby areas of a patient's brain are stimulated to determine the nature of their function. The purpose of preoperative mapping may be to locate important or non-expendable areas of the brain that are not to be sacrificed during operations such as brain tumour resections or epilepsy focus resections.

There may be many therapeutic applications for intravascular neural tissue stimulation including deep brain stimulation in the treatment of Parkinson's disease, depression, Obsessive Compulsive Disorder and Tourette's Syndrome. Advantageously such stimulation may be achieved without the need for invasive brain surgery.

It should be noted that several intravascular devices can be deployed in one or more vascular regions throughout the animal body in order to sense or stimulate neural tissue focused in one area or various areas throughout the body. Sensing neural activity in various areas may be particularly applicable when diagnosing and monitoring seizures in epilepsy.

Figure 14:
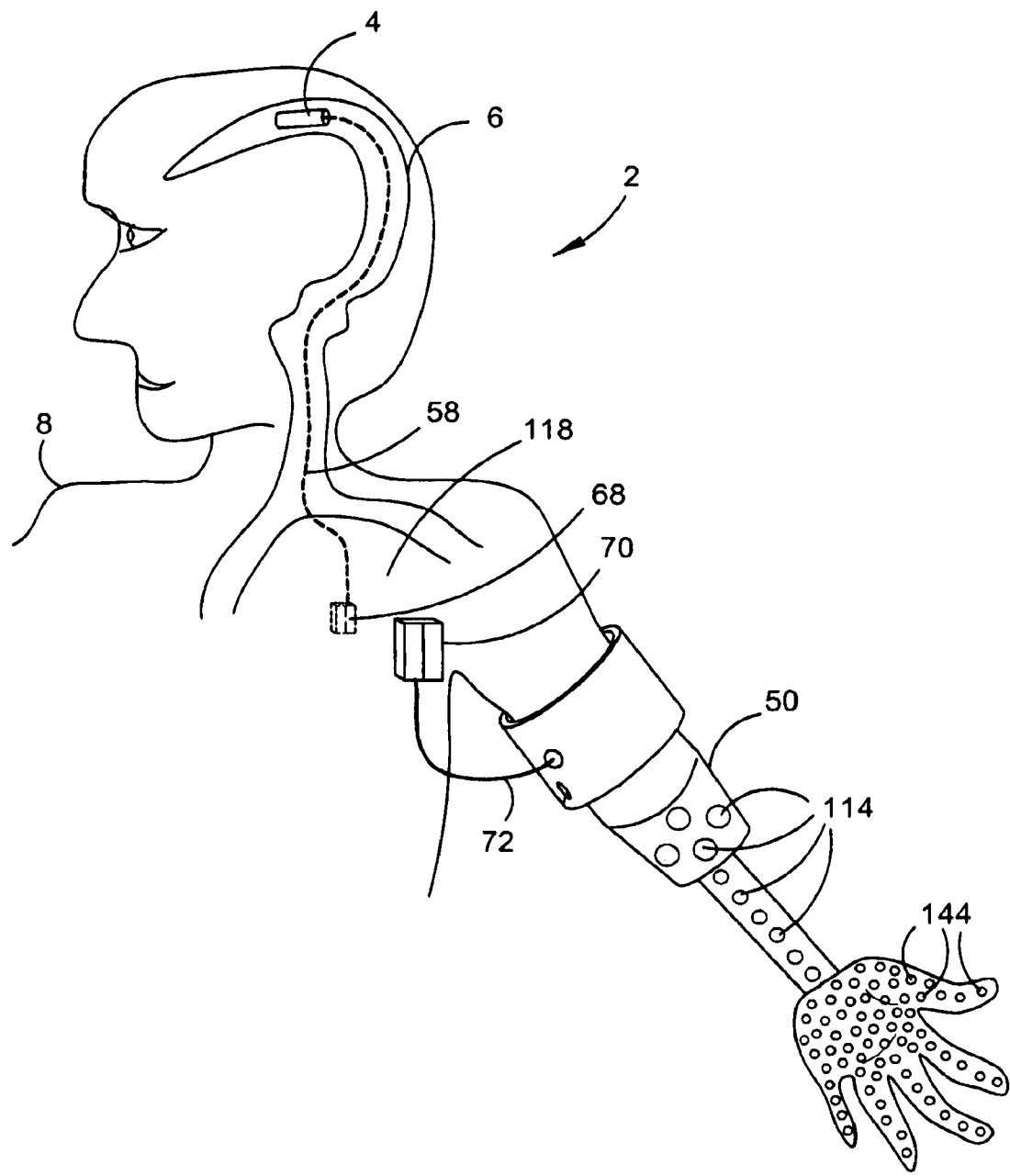
FIG. 14 is a diagram showing a subcutaneous pectorally located internal device which is wired back to the intravascular device in a brain vessel and inductively coupled to an external unit controlling a prosthetic limb.

Referring now to FIG. 14, there is shown a further system 2 comprising an internal unit 68 located subcutaneously in the left pectoral region 118 and connected by wire 58 back through the vasculature 6 to an intravascular device 4 deposited within a brain vessel 6. The system further comprises an external unit 70 mounted externally on the skin overlying the internal unit 68 and being inductively coupled therewith, the external unit being connected by wire 72 to a prosthetic limb 50.

Figure 15:
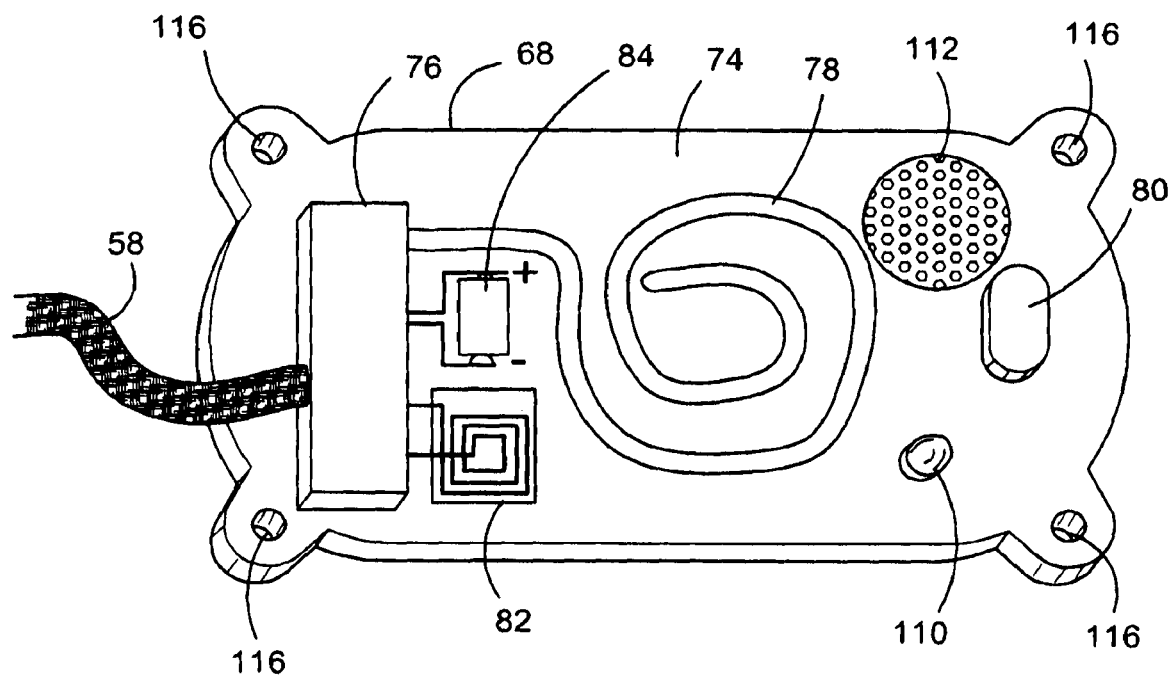
FIG. 15 is a diagram of an internal unit.

As shown in FIG. 15, the internal unit 68 comprises an internal mounting member 74 which defines suture holes 116 for fixing the unit subcutaneously. Mounted on the internal mounting member 74 is an internal microchip 76 comprising an application specific integrated circuit. Also mounted on the internal mounting member is an internal magnetic induction coil 78 connected to the internal microchip 76, as well as an internal magnet 80.

The internal unit 68 in FIG. 15 is also shown having an internal RF transmitter/receiver 82 and an internal battery or capacitor 84, although it is envisaged that the battery and RF transmitter/receiver may not be required in some versions of the internal unit, particularly where electrical and data transfer is already effectively achieved by wireless inductive coupling with the external unit. However, inclusion of a battery adapted to be charged by the inductive coupling may also be useful as a back-up energy source when the external unit is moved to location remote from the internal unit and ceases to effectively produce energy of its own.

The internal unit 68 further comprises an alert system in the form of a alert light 110 and a speaker 112, although it is envisaged that other alert devices may be used, including vibrating devices.

Figure 16:
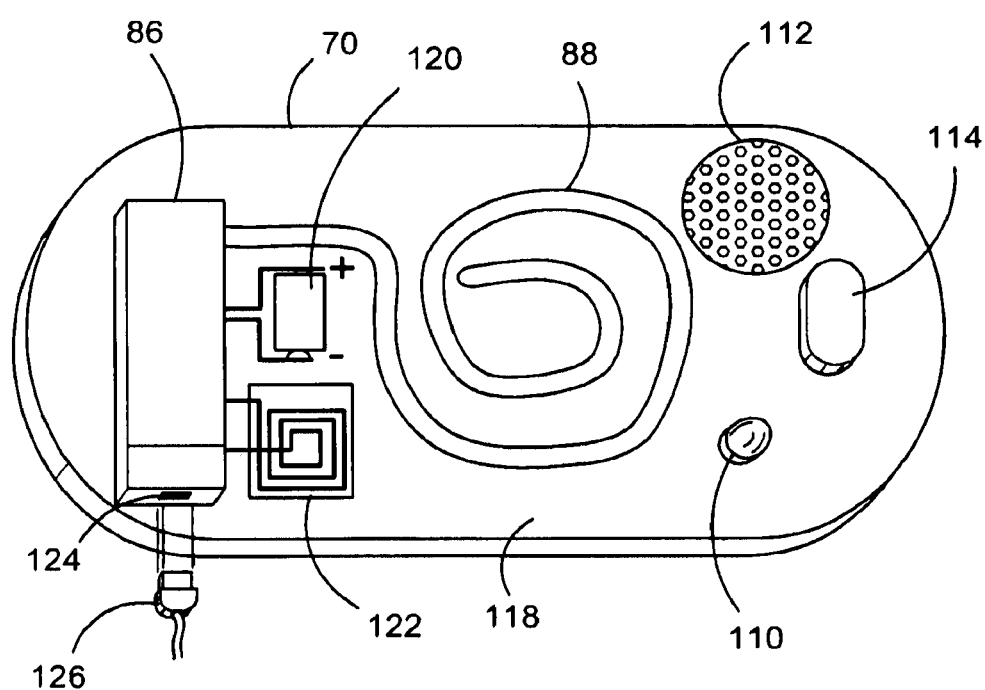
FIG. 16 is a diagram of an external unit.

FIG. 16 shows the external unit 70 which comprises an external magnet 114, external microchip 86 with application specific integrated circuit, and an external magnetic induction coil 88 wired to the microchip, all mounted on an external mounting board. The external magnetic induction coil 88 and external magnet 80 are arranged to correspond with like components of the internal unit 68.

The external unit 70 is located on the skin overlying the internal unit 68. Attraction between the internal and external magnets of the respective units facilitates achievement of optimal alignment for transmission between the internal and external magnetic induction coils.

The external unit 68 in FIG. 16 is also shown having an external RF transmitter/receiver 122 and an external battery or capacitor 120, although it is envisaged that the battery and RF transmitter/receiver may not be required in some versions of the external unit, particularly where electrical and data transfer is already effectively achieved by wireless inductive coupling with the external unit.

The external unit 70 further comprises a connection port 124 enabling connection of the external unit 70 with cable 126 which may in turn be connected to an external device such as a computer or power outlet thereby enabling wired transfer of data and energy between the external unit 70 and another external device.

Also comprised by the internal unit 69 is an alert system in the form of an alert light 110 and a speaker 112, although it is envisaged that other alert devices may be used, including vibrating devices. The alert system may be used for various alerts including in cases of low power, device or system malfunction, completed periods of monitoring or recording, or current or impending medical pathology or irregularity.

The incorporation of a power source and information processor in the internal unit version shown in FIG. 15 means that these features may potentially be omitted from the intravascular device of the system shown in FIG. 14. Thus, the deposited intravascular device in this system may be similar to intravascular device previously discussed with respect to FIG. 8, i.e. not having its own power source or microchip, but comprising electrodes 14 and a wire bundle 58 which extends down through the vasculature to connect with the microchip 76 of the internal unit.

In the system of FIG. 14, the intravascular device 4 is located in a portion of a vessel 6 adjacent the motor homunculus. In this instance, the intravascular device 4 was passed into the internal jugular vein 170 and guided up through the sigmoid sinus 172, transverse sinus 174 and into the superior sagittal sinus 178 where it is deposited. It is envisaged, however, that other routes and places of deposition may also be suitable, including places for deposition such as the cerebral veins 184 (see FIG. 23) branching off the superior sagittal sinus, other veins lying adjacent the motor cortex, the second branch of the middle cerebral artery 160 (see FIG. 22), and other arteries lying adjacent the motor cortex.

Attempted active movement of the prosthetic limb 50 by the human being 8 results in generation of action potentials in the upper limb homuncular region of the precentral gyrus. The resultant cortically originating changes in electrical potential are sensed by the electrodes 14 of the intravascular device 4 and transmitted along the wire bundle 58 to the microchip 76 of the internal unit 68.

Figure 17:
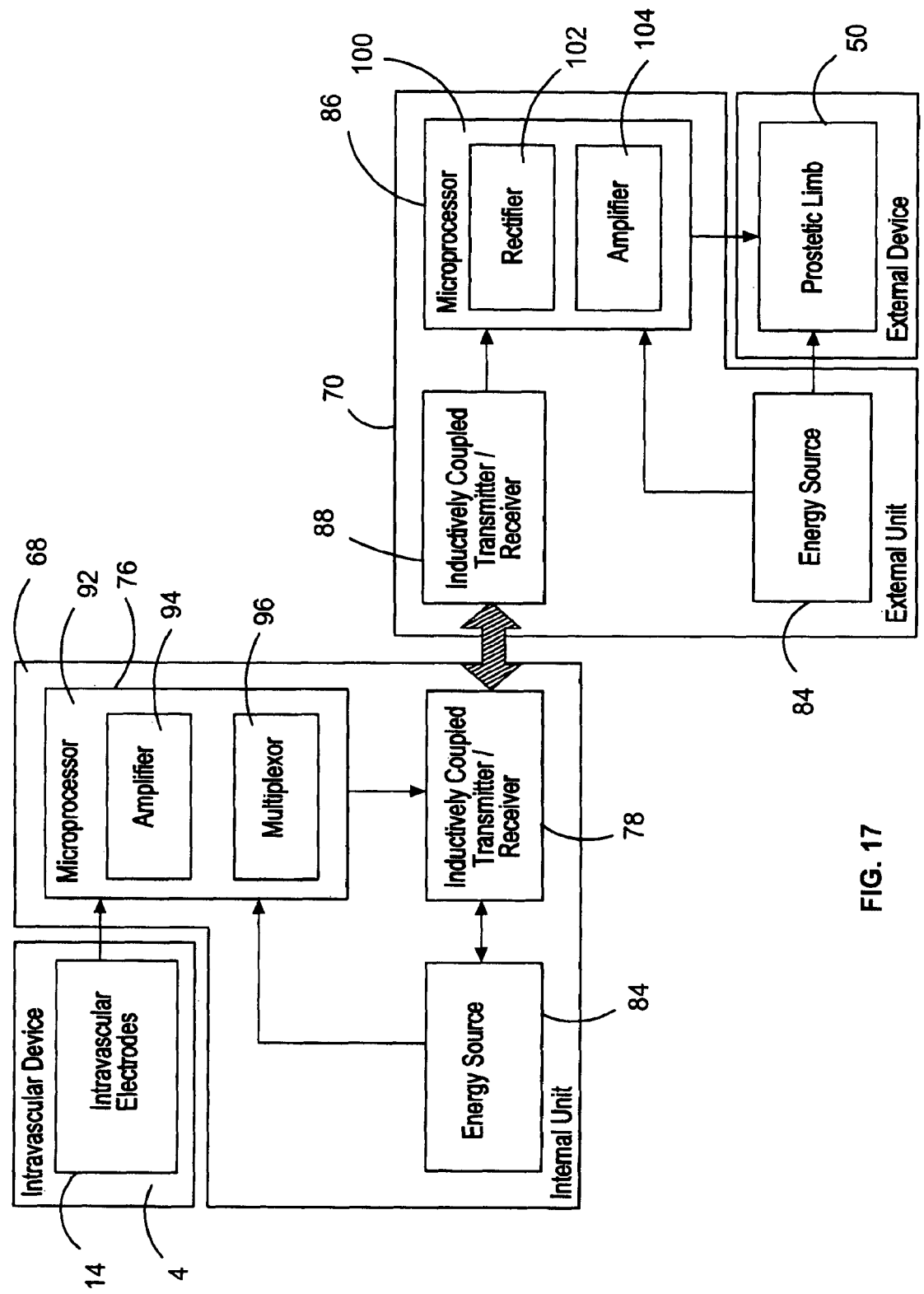
FIG. 17 is a block diagram illustrating possible electrical and data flow within and between internal and external units.

FIG. 17 illustrates possible flow of data and/or energy between the intravascular device 4, internal unit 68, external unit 70, and external device which comprises a prosthetic limb 50 in this instance.

As previously mentioned, the electrical signal passes from the electrodes 14 to the internal microchip. The internal microchip 76 comprises an application specific integrated circuit with microprocessor 92 for processing the received signal. The microchip further comprises an amplifier 94 for amplifying the signal, and a multiplexer 96 for digitally converting the signal, before the signal is passed to the internal inductive loop 78 and wirelessly transmitted through the cutaneous pectoral tissue to the external coil 88 of the external unit 70.

The external unit passes the signal through its own external microchip 98 with microprocessor 100 which decodes the signal. The external microchip further comprises a rectifier 102 for converting the signal and an amplifier 104 for amplifying the signal. The signal is decoded by the microprocessor and the decoded signal is used to control microprocessors and motors on the prosthetic limb 50, thereby causing movement of the limb to occur in accordance with the area and degree of precentral gyms activation.

The prosthetic limb comprises sensors 114 (see FIG. 14) adapted to sense touch, temperature, pressure or vibration in the area of the sensor 114. The sensors are smaller and more tightly packed anteriorly in the robotic fingers than in the robotic forearm, thereby providing more finely tuned sensation in the fingers for grasping and handling objects.

When activated, the sensors 114 send electrical signal from the prosthetic limb to the external unit where the signal is processed and conducted across the skin to the internal unit where further processing occurs, before the signal is passed up to the intravascular device 4, or another intravascular device 4, deposited adjacent the post-central gyrus. Here, the electrodes stimulate the area of brain corresponding to the signal received from the sensors 144, such that the patient is able to feel what is sensed by the prosthetic limb.

Additionally or alternatively, the signal from the sensors 114 may be passed up to another intravascular device located in a vessel adjacent the precentral gyrus. This signal causes the intravascular electrodes 14 to stimulate the adjacent neural tissue of the motor homunculus, thereby causing movement of the limb such as may reflexively occur when the muscle spindles of a natural limb are quickly stretched or the skin is burnt.

Figure 18:
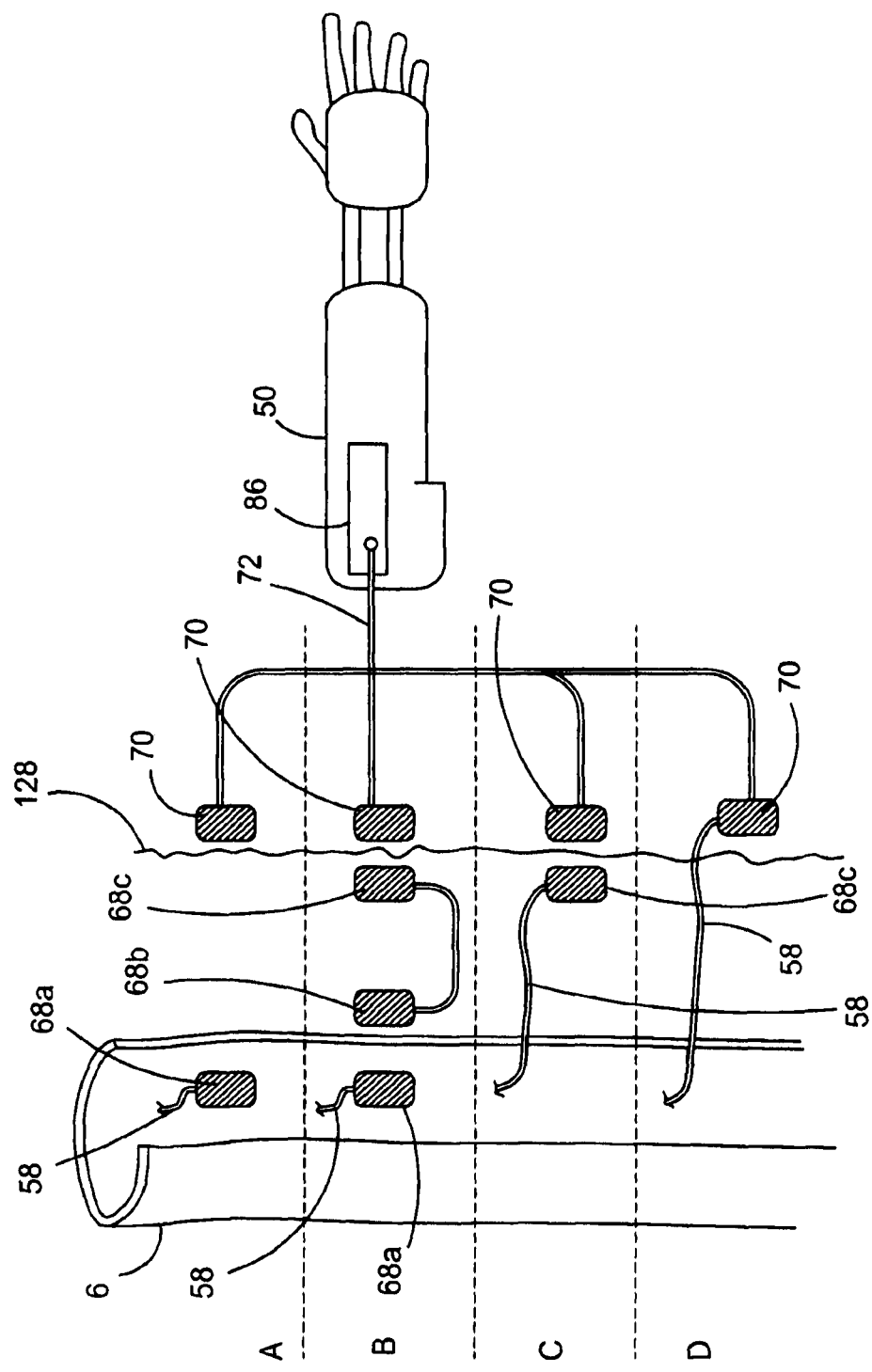
FIG. 18 is a diagram illustrating various arrangements of internal and external units.

FIG. 18 illustrates various methods of connection from the intravascular device 4 to the prosthetic limb 50 via internal and external units, 68 and 70 respectively. As was evident in the system of FIG. 14, method "C" shows a wire 58 running from an intravascular device (not shown) through the vessel 6 before piercing the vessel wall and connecting with an extravascular subcutaneous internal unit 68. The internal unit communicates wirelessly with an adjacent external unit 70 mounted on the skin 128, which external unit is wired to the prosthetic limb 50. It is envisaged that regions other than the pectoral region may also be suitable for placement of the internal and external units, such as the neck region.

Method "A" shows an intravascularly placed internal unit 68c, which is wired to an intravascular device 4 (not shown) communicating wirelessly with an external unit 70 disposed on the skin 128 and wired to the prosthetic limb 50. Rather than having a processor and wireless transmission system located on the intravascular device, this arrangement allows the processor and/or wireless transmission system to be located on the internal unit, meaning that the intravascular device may be of smaller size, and the wireless transmission system may be placed in a region which is more suitable for wireless transmission to an external unit.

Method "B" shows a double induction coupling system whereby an intravascular internal unit 68a, which is wired to an intravascular device (not shown) communicates wirelessly across the vessel wall with an adjacent proximal extravascular internal unit 68b. The internal unit 68b is in turn wired to a distal subcutaneous internal unit 68c that communicates wirelessly across the skin 128 with an external unit 70 which is mounted externally on the skin and wired to the prosthetic limb. This arrangement potentially allows for more closely coupled wireless transmissions and avoids piercing of tissues such as vessels and skin.

Method "D" provides for an intravascular device 4 (not shown) which is wired directly to an external unit 70 located on the surface of the skin, which external unit is connected by wire 72 to the prosthetic limb. Thus, no internal unit is present in this arrangement.

Figure 19:
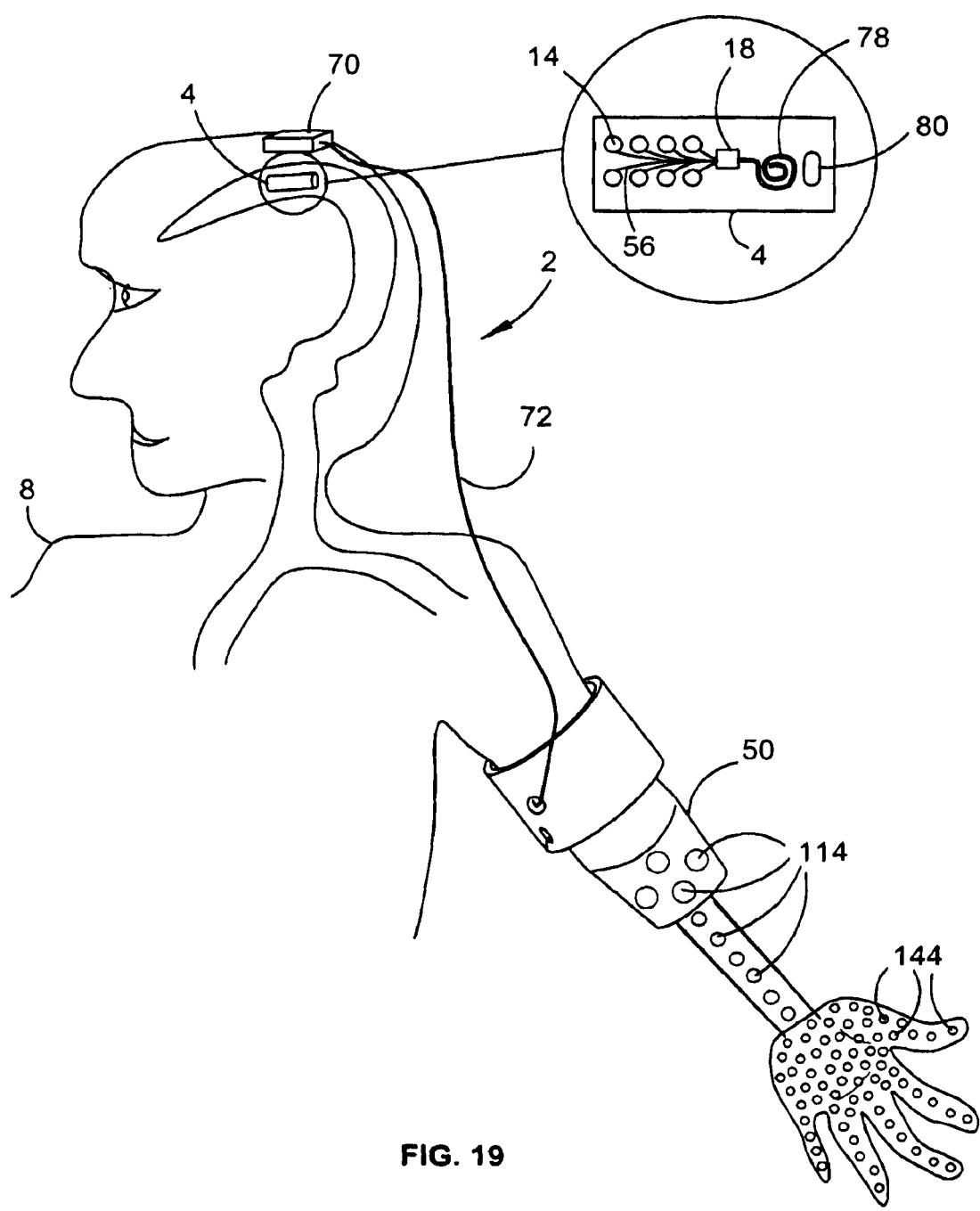
FIG. 19 diagrammatically illustrates a wireless version of the intravascular device which communicates directly with an external unit overlying an adjacent region of the skull.

Referring now to FIG. 19 there is shown a system 2 comprising a wireless version of an intravascular device 4 which is inductively coupled to an external unit placed over the skin adjacent the region of deposition of the intravascular device. As shown in the inset, intravascular device 4 comprises an array of electrodes 14 connected by wires 56 to a microchip 18 which is in turn connected to an internal magnetic induction coil 78. The intravascular device further comprises an internal magnet 80 for facilitating optimal placement of the external unit by magnetic attraction. The external unit 70 shares the same features as that shown in FIG. 16, and is connected by wire 72 to the prosthetic limb 50.

The system 2 of FIG. 19 works in a similar fashion as that shown in FIG. 14 except rather than the electrical signal received by the electrodes being passed by wire 58 down through the vasculature to an internal unit, the signal passes directly from electrode wires 56 into the microchip 18 where similar processing as occurred in the internal unit takes place. The processed signal is then transmitted via magnetic induction to the external unit 70 mounted on the adjacent portion of skin overlying the skull.

Figure 20:
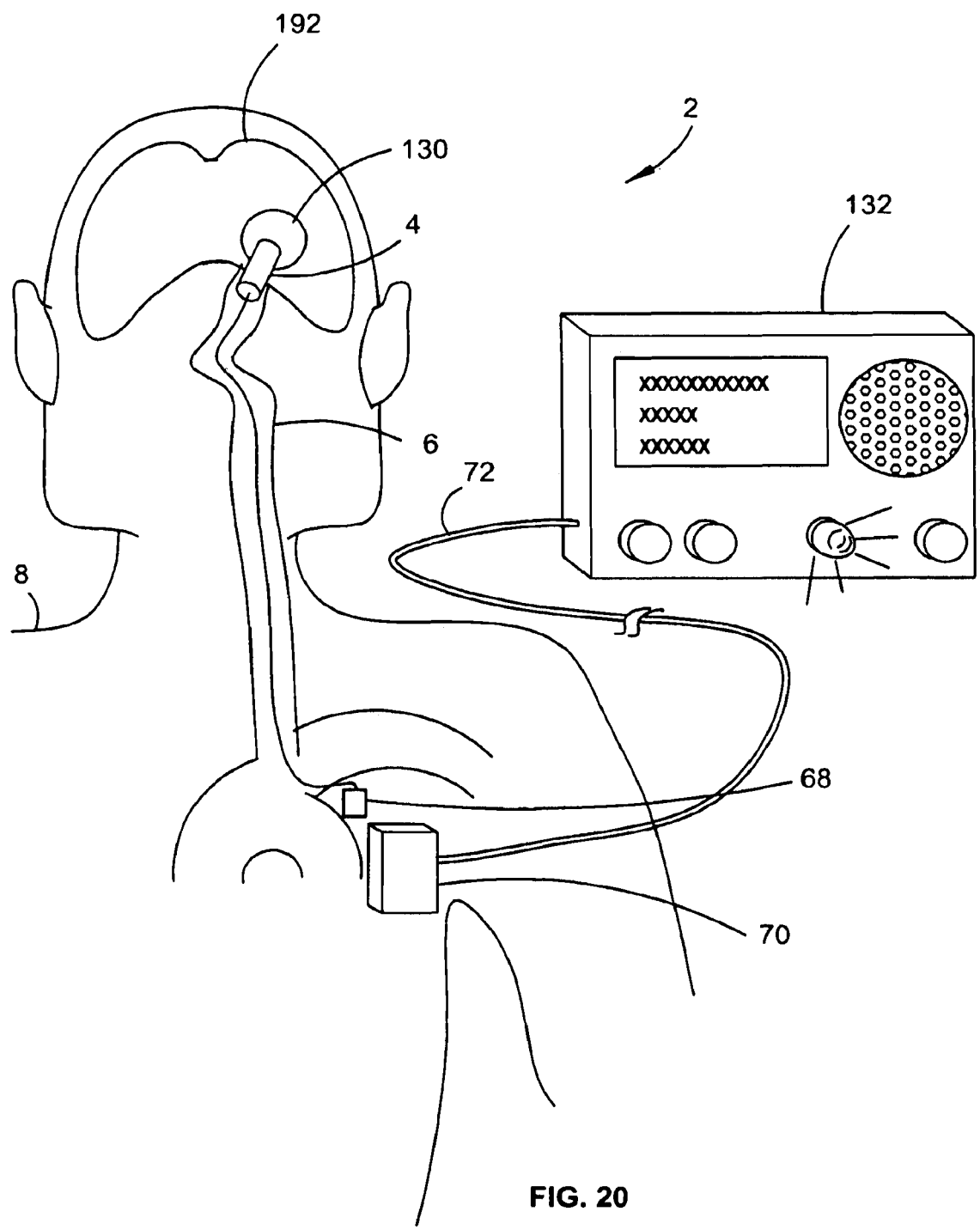
FIG. 20 is a diagram illustrating how the intravascular device may be deposited in the hippocampal region of the brain for pre-seizure detection or deep brain stimulation.

FIG. 20 shows yet another system 2 wherein the intravascular device is specifically lodged in a vessel 54 traversing the hippocampus 54. For instance, intravascular device 4 may be entered into the vascular system 6 via the cavernous sinus and passed up therethrough before being deposited in the internal cerebral vein or one of its branches 186 (see FIG. 23). Here, intravascular device can be used as an early warning seizure detection system, whereby abnormal excitation in hippocampal tissue adjacent the intravascular device is sensed by the electrodes of the device, and the electrical signal is in turn transmitted to an internal unit 68 which is located subcutaneously in the pectoral region in this instance, although it is envisaged that the wire could run directly to an external unit 70 mounted on to the outer surface of the skin. Here, an alert system in the form of an alert light 110 or speaker 112 may be activated to cause the emission of light or sound, thereby alerting the user that a seizure may be imminent, and allowing them to take necessary prophylactic action such as the ingestion of anti-epileptic drugs.

The internal unit may draw energy from an internal battery or capacitor 84 which is adapted to be charged by magnetic induction when the external units is located adjacent the internal unit. Thus, this arrangement allows the external unit to be situated remotely from the user, only being fastened to the skin overlying the internal unit when transfer of data or charging of the battery or capacitor is required. Alternatively, there may be no external unit, and the internal unit may operate on a long life battery, such as those used in cardiac pacemakers, activating alert signals when the hippocampal signal threshold is passed.

The embodiment of FIG. 20 also shows an external unit connected to a box 132 which is adapted to measure and compute signals received. In another aspect, the box 132 may be adapted to send electrical signals to the external unit, where the signals are conducted to the internal unit and passed up by wire to the intravascular device, thereby activating the electrodes to stimulate adjacent deep cortical tissue. Thus, brain stimulation may be achieved in such a fashion, with placement of the intravascular device varying depending on the region of the brain to be stimulated.

Figure 21:
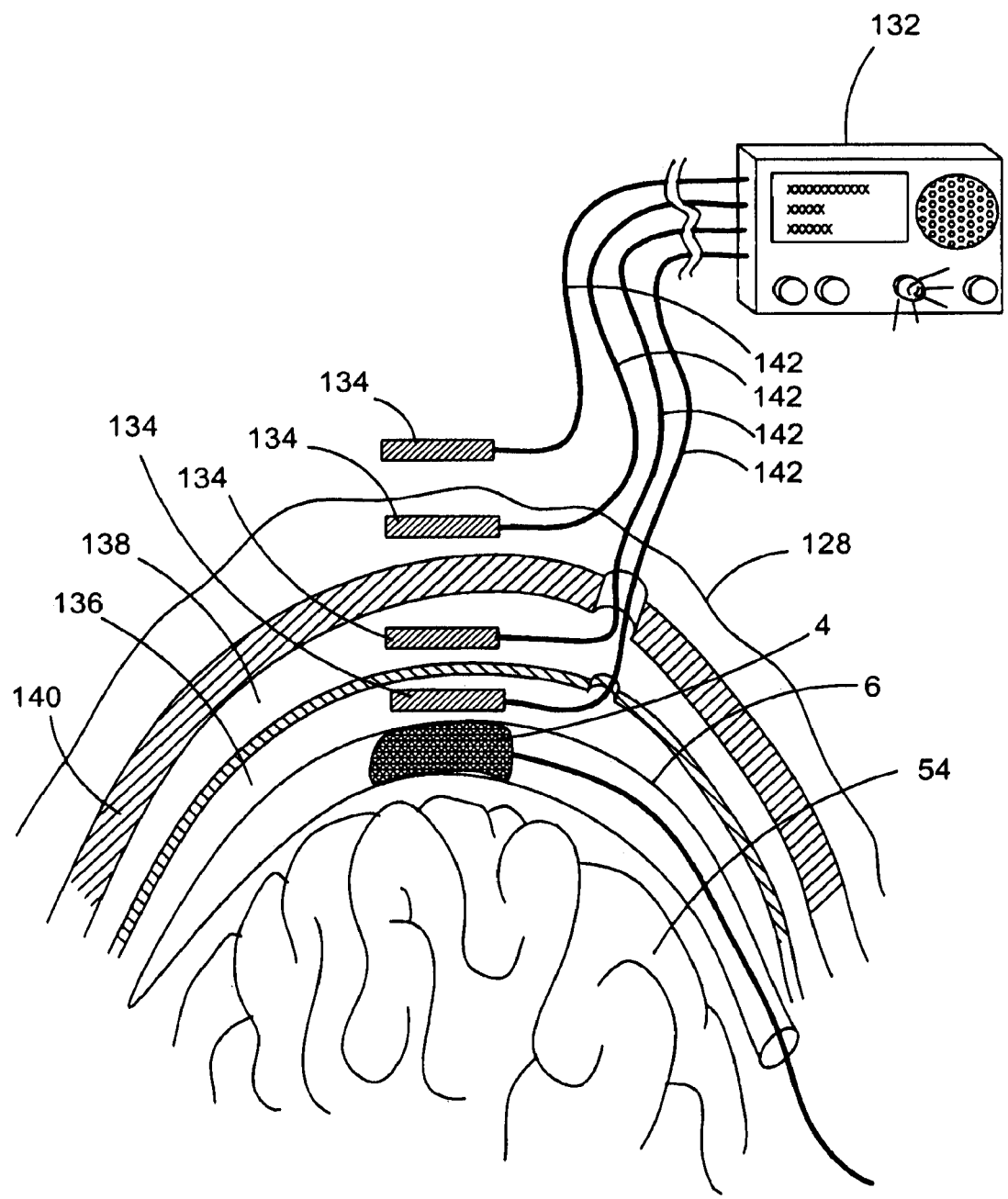
FIG. 21 is a diagram illustrating a testing procedure utilizing stimulating electrodes for mapping and identifying optimal regions for placement of the intravascular device within a vessel.

FIG. 21 illustrates how testing may be conducted to map or identify optimal placement of the intravascular device 4. For example, testing may occur preoperatively in humans prior to long-term deposition of an intravascular device, or may be performed in animals for mapping optimal locations in like structures to humans.

In the testing procedure, the intravascular device 4 is retained in a location within a vessel for testing. A hole is drilled through the skin layer, skull and dura, and stimulating electrodes 134 are inserted into the subarachnoid space 136 and subdural space 138 beneath the skull 140, sub-dermally, and externally on the skin, with each of the devices being connected by wires 142 back to an external stimulating box 132. Under control of the box 132, the electrodes 134 are used to stimulate areas of the brain which are desired to be sensed, and the signal detected by the intravascular device 4 is recorded. The procedure is then repeated with the intravascular device retained in different regions in the vessel to determine where optimal signal sensing occurs. This location may be suitable for long term deposition of an intravascular device for sensing and/or stimulating purposes.

Figure 22:
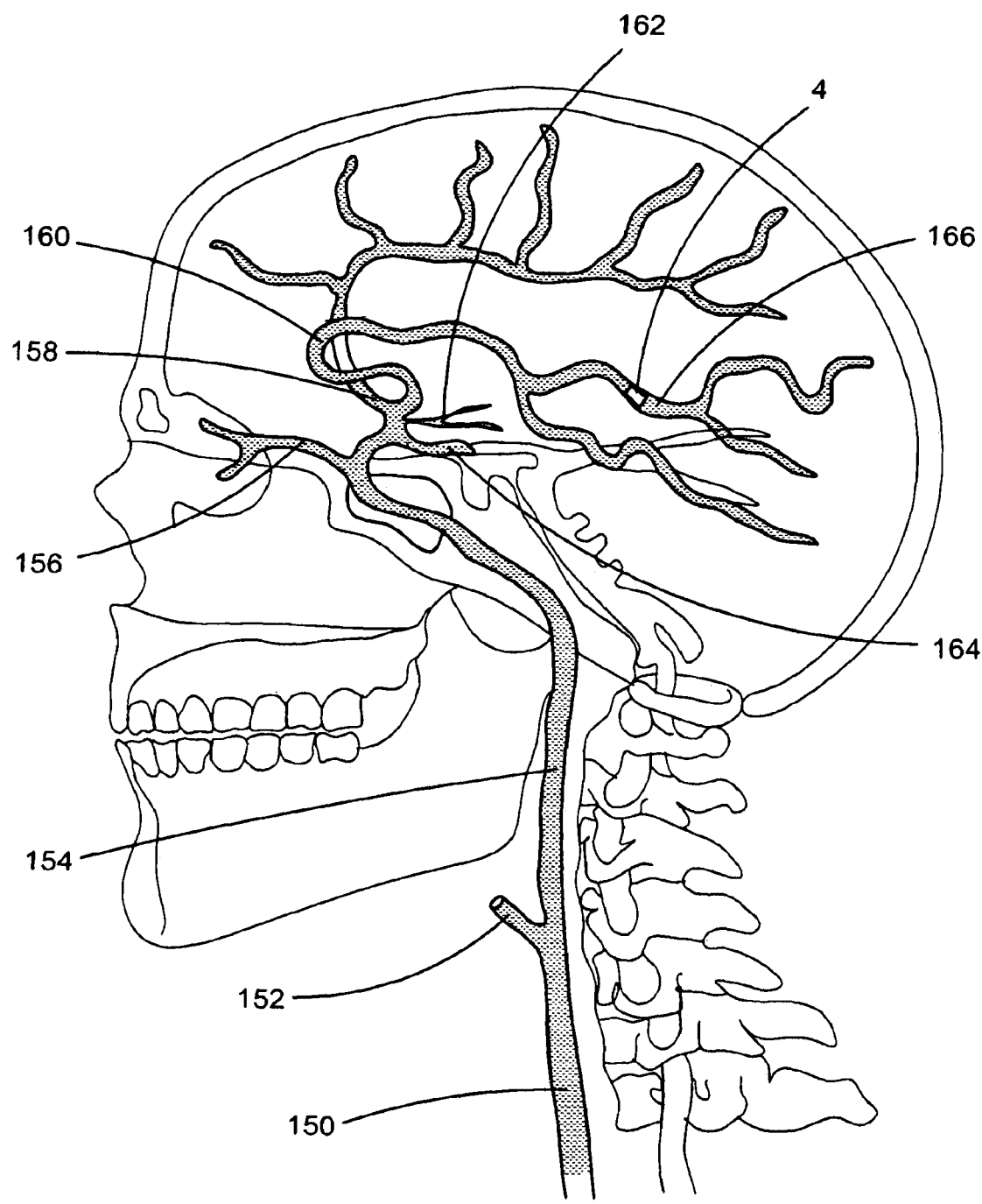
FIG. 22 illustrates arterial vasculature traversing a human brain and potential deposition sites for an intravascular device.

FIG. 22 illustrates arterial vasculature which leads to and traverses a human brain, providing potential pathways for passage, and sites for deposition, of one or more intravascular devices. Specifically referenced is the common carotid artery 150, external carotid artery 152, internal carotid artery 154, ophthalmic artery 156, anterior cerebral artery 158, middle cerebral artery 160, anterior choroidal artery 162, posterior communicating artery 164 and the second branch of the middle cerebral artery 166 in which an intravascular device 4 is deposited.

Figure 23:
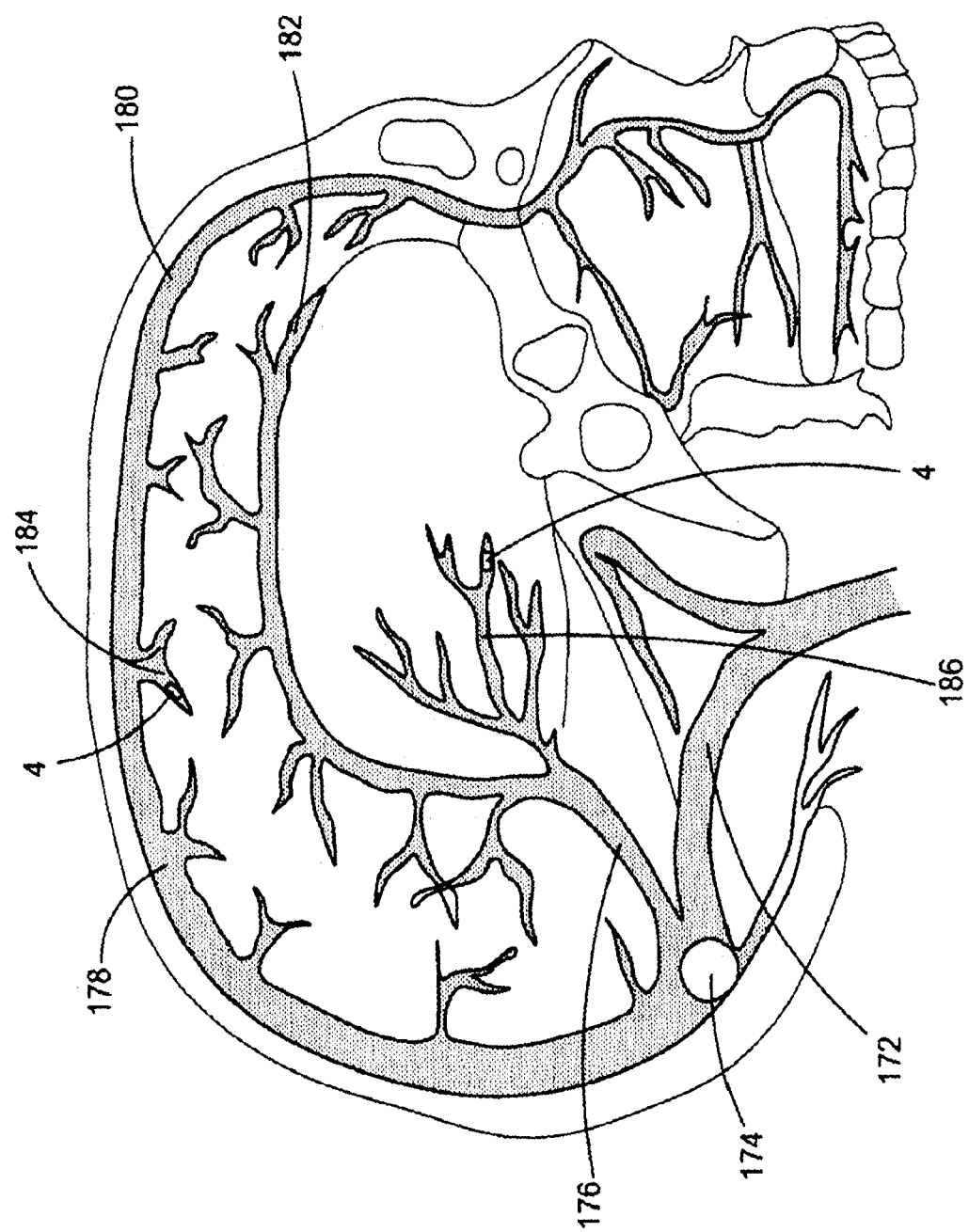
FIG. 23 illustrates venous vasculature traversing a human brain and potential deposition sites for an intravascular device.

FIG. 23 illustrates venous vasculature which leads traverses and passes from a human brain, providing potential pathways for passage, and sites for deposition, of one or more intravascular devices. Specifically referenced is the internal jugular vein 170, sigmoid sinus 172, transverse sinus 174, straight sinus 176, superior sagittal sinus 178, falx cerebri 180, inferior sagittal sinus 182, cortical veins 184, in one of which an intravascular device 4 is deposited, and internal cerebral vein 186 and its deep branches, in one of which an intravascular device 4 is deposited.

Where the terms "comprise", "comprises", "comprised" or "comprising" are used in this specification, they are to be interpreted as specifying the presence of the stated features, integers, steps or components referred to, but not to preclude the presence or addition of one or more other features, integers, steps, components to be grouped therewith.

What is claimed:

1. A method for enabling a patient to control operation of an external device using a region of a brain stimulated by the patient, the method comprising:
  advancing an intravascular device within a vasculature of the patient to a cerebral vessel in the brain of the patient, where the intravascular device comprises a stent structure having a plurality of discrete electrodes each having an electrode surface that extends parallel to a surface of the stent structure, where a plurality of wires are electrically coupled to the plurality of discrete electrodes, where the plurality of wires extends through the vasculature from the cerebral vessel to an extra-cranial vessel;
  deploying the stent structure within the cerebral vessel such that the stent structure expands to take a shape of the cerebral vessel, where expansion of the stent structure brings each electrode surface of the plurality of electrodes into engagement with a wall of the cerebral vessel without expanding or altering the shape of the electrode surface of each of the plurality of discrete electrodes, where the wall of the cerebral vessel is adjacent to a neural tissue stimulated by the patient such that the plurality of discrete electrodes sense an electrical activity in the neural tissue; and positioning an internal unit exterior to the extra-cranial vessel and in electrical communication with the plurality of wires, the internal unit configured to generate a signal, where the electrical activity from the plurality of electrodes conducts through the plurality of wires to the internal unit located exterior to the extra-cranial vessel such that the unit generates the signal in response to the electrical activity; and where the internal unit is further configured to transmit the signal to the external device so that the patient controls operation of the external device by stimulating the region of the brain.

2. The method of claim 1, where the plurality of discrete electrodes is arranged in an array.

3. The method of claim 1, where the stent structure comprises a mesh stent.

4. The method of claim 1, where the stent structure comprises a biodegradable or bioabsorbable substance.

5. The method of claim 1, where the stent structure is biased to expand.

6. The method of claim 1, wherein transmitting the signal from the internal unit to the external device comprises inductively coupling the internal unit to an external unit, where the external unit is mounted externally to the patient.

7. The method of claim 1, further comprising positioning a plurality of additional stent structures each having an array of electrodes within various regions of one or more cerebral vessels.

8. The method of claim 1, wherein the external device comprises a prosthetic limb and transmitting the signal from the internal unit causes movement of the prosthetic limb.

9. The method of claim 1, wherein the stent structure is positioned in a second branch or a third branch of a middle cerebral artery which tracks in or along a post central gyrus of the brain.

10. The method of claim 1, comprising sensing changes in the electrical activity in a pre central gyrus of the brain tissue resulting from attempted movement of natural, absent, or artificial body parts coupled to the patient.

11. The method of claim 1, further comprising transmitting a second signal from the external device to the internal unit, where the second signal is electrically conducted through the plurality of wires to the plurality of discrete electrodes to produce a stimulated electrical activity of the neural tissue.

* * * * *